United States Patent
Mccaffrey et al.

(10) Patent No.: US 10,851,418 B2
(45) Date of Patent: Dec. 1, 2020

(54) BLOOD BIOMARKERS FOR RESPIRATORY INFECTIONS

(71) Applicant: The George Washington University a Congressionally Chartered Not-for-Profit Corporation, Washington, DC (US)

(72) Inventors: Timothy A. Mccaffrey, Silver Spring, MD (US); Lakhmir S. Chawla, San Diego, CA (US)

(73) Assignee: THE GEORGE WASHINGTON UNIVERSITY A CONGRESSIONAL CHARTERED NOT-FOR-PROFIT CORPORATION, Washington, DC (US)

( * ) Notice: Subject to any disclaimer, the term of this patent is extended or adjusted under 35 U.S.C. 154(b) by 38 days.

(21) Appl. No.: 15/542,863

(22) PCT Filed: Jan. 12, 2016

(86) PCT No.: PCT/US2016/012981
§ 371 (c)(1),
(2) Date: Jul. 11, 2017

(87) PCT Pub. No.: WO2016/115089
PCT Pub. Date: Jul. 21, 2016

(65) Prior Publication Data
US 2017/0369946 A1    Dec. 28, 2017

Related U.S. Application Data

(60) Provisional application No. 62/102,350, filed on Dec. 1, 2015.

(51) Int. Cl.
| | | |
|---|---|---|
| *C12Q 1/6883* | (2018.01) | |
| *C12N 15/113* | (2010.01) | |
| *G16B 25/00* | (2019.01) | |
| *G16B 40/00* | (2019.01) | |
| *A61K 31/7105* | (2006.01) | |

(52) U.S. Cl.
CPC ........ *C12Q 1/6883* (2013.01); *A61K 31/7105* (2013.01); *C12N 15/113* (2013.01); *G16B 25/00* (2019.02); *G16B 40/00* (2019.02); *C12Q 2600/158* (2013.01)

(58) Field of Classification Search
None
See application file for complete search history.

(56) References Cited

U.S. PATENT DOCUMENTS

| | | | |
|---|---|---|---|
| 7,550,300 B1 | 6/2009 | Lundergan et al. | |
| 2005/0214217 A1* | 9/2005 | Levite ................ | A61K 49/0002 424/9.1 |
| 2012/0329666 A1 | 12/2012 | Steele et al. | |
| 2013/0011933 A1* | 1/2013 | Nakamura ........... | C12Q 1/6886 436/501 |
| 2013/0065972 A1* | 3/2013 | Dent ...................... | C12Q 1/686 514/789 |
| 2013/0190194 A1* | 7/2013 | Tang .................... | C12Q 1/6809 506/9 |
| 2014/0179806 A1 | 6/2014 | Kain et al. | |
| 2014/0233282 A1* | 8/2014 | Ohoka .................... | H02M 1/14 363/39 |

FOREIGN PATENT DOCUMENTS

WO    WO 2012/037061 A2    3/2012

OTHER PUBLICATIONS

International Preliminary Report on Patentability in International Application No. PCT/2016/012981, dated Jul. 18, 2017.
Almansa et al, "Critical COPD respiratory illness is linked to increased transcriptomic activity of neutrophil proteases genes," BMC Res Notes 5: 401 (2012).
Berkestedt et al., "Elevated plasma levels of antimicrobial polypeptides in patients with severe sepsis," J Innate Immun 2(5): 478-482 (2010).
Bostrom et al., "Resistin is stored in neutrophil granules being released upon challenge with inflammatory stimuli," Biochim Biophys Acta 1793(12): 1894-1900 (2009).
Johansson et al., "Neutrophil-derived hyperresistinemia in severe acute streptococcal infections," J Immunol 183(6): 4047-4054 (2009).
Lozano et al. "Global and regional mortality from 235 causes of death for 20 age groups in 1990 and 2010: a systematic analysis for the Global Burden of Disease Study 2010," Lancet 380(9859): 2095-2128 (2012).
Macdonald et al., "Sustained elevation of resistin, NGAL and IL-8 are associated with severe sepsis/septic shock in the emergency department," PLoS One 9(10): e110678 (2014).
Sekine, "Panning of multiple subsets of leukocytes on antibody-decorated poly(ethylene) glycol-coated glass slides," Journal of immunological methods 313(1-2): 96-109 (2006).
Sethu et al., "Microfluidic isolation of leukocytes from whole blood for phenotype and gene expression analysis," Anal Chem 78(15): 5453-5461 (2006).
Toma et al., "Single-Molecule Long-Read 16S Sequencing to Characterize the Lung Microbiome from Mechanically Ventilated Patients with Suspected Pneumonia," J Clin Microbiol 52(11): 3913-3921 (2014).
International Search Report in International Application No. PCT/US2016/012981, filed Jan. 12, 2016.

(Continued)

*Primary Examiner* — Carla J Myers
(74) *Attorney, Agent, or Firm* — Venable LLP; Henry J. Daley; Miguel A. Lopez

(57) ABSTRACT

Methods and kits for diagnosing and/or treating a lower respiratory infection in a subject include obtaining a biological sample from the subject; detecting RNA expression levels of one or more biomarkers in the biological sample and comparing the expression levels of the one or more three biomarkers to at least one invariant control marker wherein an increase or decrease in the level of expression of the one or more biomarkers as compared to the at least one invariant control marker is indicative of a lower respiratory infection.

19 Claims, 1 Drawing Sheet

(56) References Cited

OTHER PUBLICATIONS

Christ-Crain et al., "Biomarkers in respiratory tract infections: diagnostic guides to antibiotic prescription, prognostic markers and mediators" European respiratory journal, 2007, pp. 556-573.
Shah et al., "Biomarkers for predicting illness severity in children with acute lower respiratory tract infections" Pediatric infectious diseases society, 2014 pp. 189-191.
Blasi et al., "Biomarkers in lower respiratory tract infections," Pulmonary Pharmacology & Therapeutics, vol. 23, pp. 501-507.
Jendeberg et al., "Antimicrobial peptide plasma concentrations in patients with community-acquired pneumonia," Scand J Infect Dis 45(6): 432-437 (2013).
Kunnari et al., "The expression of human resistin in different leucocyte lineages is modulated by LPS and TNFalpha," Regul Pept 157(1-3): 57-63 (2009).
Li, "Miniature optofluidic darkfleld microscope for biosensing," SPIE Ultrafast Nonlinear Imaging and Spectroscopy, 9815:15 (2014).
Li et al., "A smartphone controlled handheld microfluidic liquid handling system," Lab Chip 14(20): 4085-4092 (2014).

\* cited by examiner

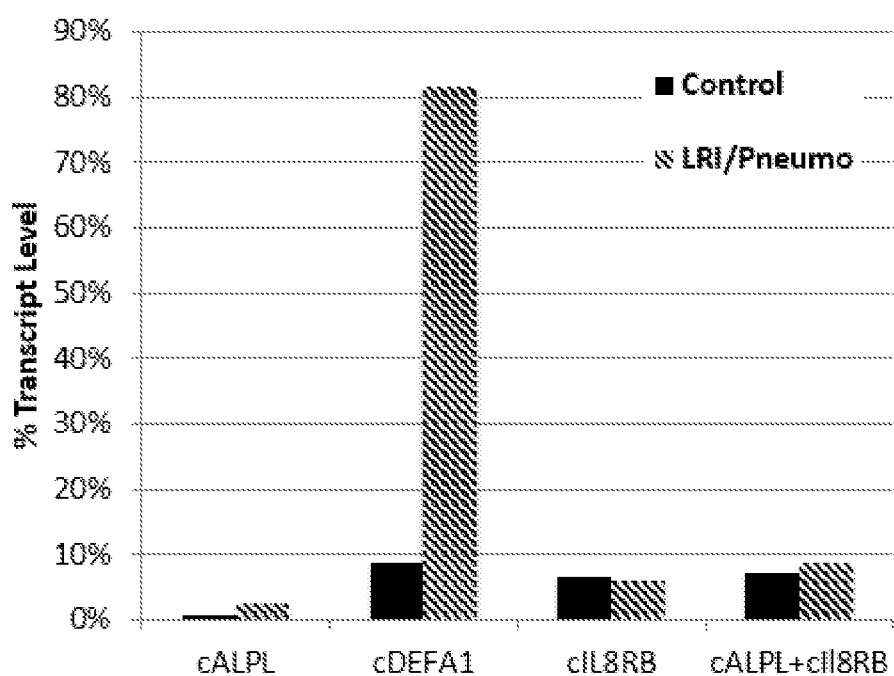

BLOOD BIOMARKERS FOR RESPIRATORY INFECTIONS

CROSS-REFERENCE OF RELATED APPLICATION

This application is a U.S. National Phase Application under 35 U.S.C. § 371 of PCT/US2016/012981, filed Jan. 12, 2016, the entire content of which is hereby incorporated by reference and this application claims priority to U.S. Provisional Application No. 62/102,350 filed Jan. 12, 2015, the entire contents of which are hereby incorporated by reference.

BACKGROUND

Technical Field

The field of the currently claimed embodiments of this invention relate to methods and kits for assessing and treating lower respiratory infections in a subject, and more particularly to assessing and treating lower respiratory infections in a subject using the analysis of biomarkers isolated from the subject.

Discussion of Related Art

Worldwide, communicable diseases account for ~10 million deaths per year [1]. An important step in controlling this problem is developing simple, inexpensive, and rapid diagnostics. Attempts to develop assays based on circulating biomarkers for infection or inflammation in plasma have been largely unsuccessful. A major weakness in this approach is that the key biomarkers are retained within the activated immune cells, particularly primed or activated neutrophils.

Of the 10 million deaths from communicable diseases, the largest category are lower respiratory infections (LRI), such as influenza and pneumonia, accounting for 2.8 M deaths per year [1]. By comparison, HIV-related diseases are a close second, with 2.6 M, but diarrheal diseases cause half as many deaths (1.4 M). Surprisingly, fever and elevated white blood cell count (WBC) are very poor metrics of pneumonia. Fever, for instance, does not occur when an infection is highly localized from the immune system, as occurs in encapsulated lung infections, such as TB. Likewise, other bacteria can form 'biofilms' in which they fuse together (i.e. fusobacteria), and secrete viscous protective coatings that can hinder immune cell response and antibiotic penetration. Further, fever is easily masked by anti-inflammatory medications such as aspirin. Importantly, even if present, fever and elevated WBC do not detect whether the person has a viral versus bacterial infection, a critical factor in the decision whether to use antibiotics or not. In developing countries, and even in rural areas of developed countries, access to imaging equipment, such as X-ray or computed tomography (CT), can be limited. Often, a stethoscope is the only available means to diagnose pulmonary dysfunction, but it has limited ability to distinguish infections from allergy, asthma, or bronchitis and depends primarily on the clinical skills and knowledge of the healthcare personnel.

There is a medical need for a high sensitivity test for infections. There is a growing list of diagnostics that detect specific infections, such as streptococci, sometimes at the point of care. Surprisingly however, there are no commercial blood tests that accurately detect infections in a general way, which could then be used to justify tests for specific pathogens. Recent studies, have described a method for using next-generation sequencing (NGS) to specifically identify the pathogens within a sample of sputum from intubated ICU patients [2]. However, it costs >$300 per test and takes days, without actually knowing whether the patient has a bacterial infection versus bronchial inflammation. Thus, there is a great need for a highly sensitive, but pathogen-agnostic test for internal infections of, for example, the lungs, appendix, central nervous system (CNS), kidneys, and other organs. Once a test is positive, then it is worthwhile to identify the pathogen, whether viral or bacterial, and determine its antibiotic sensitivity.

SUMMARY

Embodiments of the present invention include a method of diagnosing a lower respiratory infection in a subject, including the steps: obtaining a biological sample from the subject; detecting expression levels of one or more biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; and determining the expression levels of the one or more biomarkers by comparing the expression levels of the at least one or more biomarkers to at least one invariant control marker wherein an increase or decrease in the level of expression of one or more biomarkers as compared to the at least one invariant control marker is indicative of a lower respiratory infection.

Embodiments of the present invention include a method of treating a lower respiratory infection in a subject, including the steps of: obtaining a biological sample from the subject; detecting expression levels of one or more biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; determining an increase or decrease in the expression levels of said one or more biomarkers by comparing the expression levels of said one or more biomarkers to at least one invariant control marker wherein an increase or decrease of at least three-fold in the level of expression of said at one or more biomarkers as compared to the at least one invariant control marker is indicative of a lower respiratory infection; and treating the subject for a lower respiratory infection.

Embodiments of the present invention include a kit for use in diagnosing a lower respiratory infection in a subject comprising: agents that specifically bind one or more biomarkers selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; agents that specifically bind to at least one invariant control marker; a container for housing said agents; and instructions for use of the agents for determining an increase or decrease in the expression levels of said one or more biomarkers by comparing the expression levels of said one or more biomarkers to said at least one invariant control marker wherein an increase or decrease in the level of expression of said one or more biomarkers as compared to the at least one invariant control marker is indicative of a lower respiratory infection. In such embodiments, the agents that bind to the biomarkers and/or the invariant control marker bind to nucleotide residues or versions and/or to peptide versions, motifs or residues or amino acid residues of the biomarkers and invariant control marker.

Embodiments of the present invention include a method of diagnosing a lower respiratory infection in a subject comprising: obtaining a biological sample from said subject; and contacting the biological sample from said subject with a kit for use in diagnosing a lower respiratory infection in a subject.

Embodiments of the present invention include a method of treating a lower respiratory infection in a subject comprising: obtaining a biological sample from said subject; contacting the biological sample from said subject with a kit for use in diagnosing a lower respiratory infection in a subject; and treating the subject for a lower respiratory infection by administering antibiotics to said subject, administering antivirals to said subject, administering anti-inflammatories to said subject, or a combination thereof.

BRIEF DESCRIPTION OF THE DRAWINGS

Further objectives and advantages will become apparent from a consideration of the description, drawings, and examples.

FIG. 1 is a graph showing biomarker levels in suspected lower respiratory infection and/or pneumonia patients versus control subjects.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention include an innovative method for diagnosing infectious diseases. An example based on an embodiment of the current invention uses the example of pneumonia, with a blood biomarker test based on independently confirmed, genomically-derived markers. In some embodiments, two major innovations are employed: 1) instead of soluble markers, the person's own circulating cells are used as the 'canary in the mine' to sense the pathogen, and 2) solid-phase capture of specific cells, combined with specific fluorochromes used to create a small, sensitive, inexpensive, and rapid assay for infections.

The genomic-scale RNA expression screens of circulating cells described herein reveal strong cellular markers of pulmonary infections. In some embodiments, the RNA biomarkers are detectable in a handheld nanophotonic assay of whole cells, and are also expressed as changes in the proteins they encode (e.g. amount or activity). The biomarkers described herein can be employed in any of a variety of conventional assays. Although embodiments described herein are directed to the detection of pneumonia, the markers and assays can also be used to diagnose other types of infections, and can be readily adapted for other specific applications, such as appendicitis (e.g. caused by an infection), CNS infections, parasitic infections, and any situation where the immune system detects a pathogen.

Some embodiments of the present invention include methods and kits for assessing and treating lower respiratory infections in a subject, and more particularly to assessing and treating lower respiratory infections in a subject using the analysis of biomarkers isolated from the subject.

In some embodiments, the invention relates to a method of diagnosing a lower respiratory infection in a subject, including the steps: obtaining a biological sample from the subject; detecting expression levels of one or more biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; and determining the expression levels of the one or more biomarkers by comparing the expression levels of the one or more biomarkers to at least one invariant control marker wherein an increase or decrease in the level of expression of the one or more biomarkers as compared to the at least one invariant control marker is indicative of a lower respiratory infection.

In some embodiments, the invention relates to a method of diagnosing a lower respiratory infection in a subject, including the steps: obtaining a biological sample from the subject; detecting expression levels of at least three biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; and determining the expression levels of the at least three biomarkers by comparing the expression levels of the at least three biomarkers to at least one invariant control marker wherein an increase or decrease in the level of expression of the at least three biomarkers as compared to the at least one invariant control marker is indicative of a lower respiratory infection.

Some embodiments of the present invention relate to a method of diagnosing a lower respiratory infection in a subject comprising calculating a biomarker infection score from an increase or decrease in the expression levels of one or more biomarkers and comparing said biomarker infection score to a control score.

Some embodiments of the present invention relate to a method of diagnosing a lower respiratory infection in a subject comprising determining the expression levels of one or more biomarkers and at least one invariant control marker by using a multivariate prediction model to determine if a pattern of expression of said one or more biomarkers is indicative of a lower respiratory infection.

Some embodiments of the present invention relate to a method of diagnosing a lower respiratory infection in a subject wherein a blood sample is used as a biological sample.

Some embodiments of the present invention relate to a method of diagnosing a lower respiratory infection in a subject comprising isolating immune cells from a blood sample.

Some embodiments of the present invention relate to a method of diagnosing a lower respiratory infection in a subject comprising isolating neutrophils, T-cells, or a combination thereof from the subject.

Some embodiments of the present invention relate to a method of diagnosing a lower respiratory infection in a subject comprising detecting expression levels of one or more biomarkers by measuring RNA levels of the one or more biomarkers.

Some embodiments of the present invention relate to a method of diagnosing a lower respiratory infection in a subject comprising measuring RNA levels of one or more biomarkers by using fluorescently-labeled probes complementary to the one or more biomarkers, a ligase-based assay, reverse transcriptase and polymerase chain reaction, RNA sequencing, or cDNA microarray.

Some embodiments of the present invention relate to a method of diagnosing a lower respiratory infection in a subject comprising detecting expression levels of one or more biomarkers selected from the group consisting of bactericidal/permeability-increasing protein, myeloperoxidase, resistin, G antigen 12F, CD40 molecule TNF receptor superfamily member 5 transcript variant 2 and splicing factor 1 transcript variant 4.

Some embodiments of the present invention relate to a method of diagnosing a lower respiratory infection in a subject comprising detecting expression levels of one or more biomarkers selected from the group consisting of alkaline phosphatase liver isoform (ALPL), interleukin-8 receptor-beta (IL8RB), and Defensin alpha 1.

Some embodiments of the present invention relate to a method of diagnosing a lower respiratory infection in a subject comprising detecting expression levels of one or more biomarkers and at least one invariant control marker selected from the group consisting of Spi-B transcription factor, protein phosphatase 1 regulatory subunit 21 (PPP1R21, KLRAQ1), mitogen-activated protein kinase kinase kinase 7 (MAP3K7, TAK1), olfactory receptor family 51 subfamily member 1 (OR51M1), BCL2 antagonist/killer (BAK1), and adenosine deaminase, RNA-specific (ADAR1).

Some embodiments of the present invention include a method of treating a lower respiratory infection in a subject, including the steps of: obtaining a biological sample from the subject; detecting expression levels of one or more biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; determining an increase or decrease in the expression levels of said one or more biomarkers by comparing the expression levels of said one or more biomarkers to at least one invariant control marker wherein an increase or decrease in the level of expression of said one or more biomarkers as compared to the at least one invariant control marker is indicative of a lower respiratory infection; and treating the subject for a lower respiratory infection.

Some embodiments of the present invention include a method of treating a lower respiratory infection in a subject, including the steps of: obtaining a biological sample from the subject; detecting expression levels of at least three biomarkers in the biological sample selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; determining an increase or decrease in the expression levels of said at least three biomarkers by comparing the expression levels of said at least three biomarkers to at least one invariant control marker wherein an increase or decrease in the level of expression of said at least three biomarkers as compared to the at least one invariant control marker is indicative of a lower respiratory infection; and treating the subject for a lower respiratory infection.

Some embodiments of the present invention relate to a method of treating a lower respiratory infection in a subject, wherein treating the subject for a lower respiratory infection comprises administering antibiotics to said subject, administering antivirals to said subject, administering anti-inflammatories to said subject, or a combination thereof.

Some embodiments of the present invention relate to a method of treating a lower respiratory infection in a subject by calculating a biomarker infection score from said increase or decrease in the expression levels of said one or more biomarkers and comparing said biomarker infection score to a control score.

Some embodiments of the present invention relate to a method of treating a lower respiratory infection in a subject by determining an increase or decrease in the expression levels of one or more biomarkers comprising using a multivariate prediction model to determine if a pattern of expression of said one or more biomarkers is indicative of a lower respiratory infection.

Some embodiments of the present invention relate to a method of treating a lower respiratory infection in a subject by obtaining a blood sample from the subject and determining an increase or decrease in the expression levels of one or more biomarkers.

Some embodiments of the present invention relate to a method of treating a lower respiratory infection in a subject including isolating immune cells from a blood sample from the subject.

Some embodiments of the present invention relate to a method of treating a lower respiratory infection in a subject comprising isolating neutrophils, T-cells, or a combination thereof from the subject.

Some embodiments of the present invention relate to a method of treating a lower respiratory infection in a subject comprising detecting expression levels of one or more biomarkers by measuring RNA levels of said one or more biomarkers.

Some embodiments of the present invention relate to a method of treating a lower respiratory infection in a subject comprising measuring RNA levels of one or more biomarkers by using fluorescently-labeled probes complementary to the said biomarkers, a ligase-based assay, reverse transcriptase and polymerase chain reaction, RNA sequencing or cDNA microarray.

Some embodiments of the present invention relate to a method of treating a lower respiratory infection in a subject comprising determining expression levels of one or more biomarkers selected from the group consisting of bactericidal/permeability-increasing protein, myeloperoxidase, resistin, G antigen 12F, CD40 molecule TNF receptor superfamily member 5 transcript variant 2, and splicing factor 1 transcript variant 4.

Some embodiments of the present invention relate to a method of treating a lower respiratory infection in a subject comprising determining expression levels of one or more biomarkers selected from the group consisting of defensin alpha-1, alkaline phosphatase liver isoform (ALPL), interleukin-8 receptor beta (IL8RB).

Some embodiments of the present invention relate to a method of treating a lower respiratory infection in a subject comprising determining expression levels of one or more biomarkers by comparing the expression levels of the one or more biomarkers to at least one invariant control marker selected from the group consisting of Spi-B transcription factor, protein phosphatase 1 regulatory subunit 21 (PPP1R21, KLRAQ1), mitogen-activated protein kinase kinase kinase 7 (MAP3K7, TAK1), olfactory receptor family 51 subfamily member 1 (OR51M1), BCL2 antagonist/killer (BAK1), and adenosine deaminase, RNA-specific (ADAR1).

Some embodiments of the present invention include a kit for use in diagnosing a lower respiratory infection in a subject comprising: agents that specifically bind one or more biomarkers selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; agents that specifically bind to at least one invariant control marker; a container for housing said agents; and instructions for use of the agents for determining an increase or decrease in the expression levels of said one or more biomarkers by comparing the expression levels of said one or more biomarkers to said at least one invariant control marker wherein an increase or decrease in the level of expression of said one or more biomarkers as compared to the at least one invariant control marker is indicative of a lower respiratory infection.

Some embodiments of the present invention include a kit for use in diagnosing a lower respiratory infection in a subject comprising: agents that specifically bind at least three biomarkers selected from the group consisting of Neutrophil defensin 1 precursor, Defensin alpha 1, LOC653600, defensin alpha 1B, Src homology 2 domain containing transforming protein 3, myeloperoxidase, lipocalin 2, cathepsin G, bactericidal/permeability-increasing protein, lactotransferrin (LTF), solute carrier family 22 member 2, methyltransferase like 7B, resistin, zinc finger protein 90, family with sequence similarity 46 member C, solute carrier family 7 member 5, aminolevulinate delta-synthase 2,5'-nucleotidase domain containing 2, LOC646021, G antigen 12F, LOC100133075, hypothetical protein FLJ23865, RST17329 Athersys RAGE Library cDNA, hypothetical protein LOC339047 transcript variant 74, CD40 molecule TNF receptor superfamily member 5 transcript variant 2, splicing factor 1 transcript variant 4, synaptophysin-like 1 transcript variant 1, selenoprotein P plasma 1 transcript variant 1, cDNA DKFZp779F0411, LOC643037, SH3-domain GRB2-like (endophilin) interacting protein 1, microRNA 940, PR domain containing 12, IMAGE clone 15667343, LOC100128771, LOC732387, region containing hypothetical protein LOC283970 transcript variant 2 LOC643943, hypothetical protein LOC100129705, LOC728522, regulator of G-protein signaling 20 transcript variant 1, kelch domain containing 1, LOC100134669, tripartite motif-containing 34 transcript variant 2, ribosomal protein L10-like, LOC100129929, LOC402377, LOC642073, zinc finger protein 461, creatine kinase mitochondrial 1B, yy43f04.s1 Soares melanocyte 2NbHM cDNA clone, KIAA1045, ZNF788, primary neuroblastoma clone:Nbla10527, processing of precursor 5 ribonuclease P/MRP subunit transcript variant 2, myelin transcription factor 1-like, neuroblastoma breakpoint family member 7, phospholipase C-like 1, LOC391761, LOC646498, solute carrier family 7 member 6 transcript variant 2, LOC100134648, neuroblastoma breakpoint family member 1 transcript variant 16, absent in melanoma 1-like, EPS8-like 2, angiopoietin-like 6, LOC645743, V-set and transmembrane domain containing 2A, chemokine binding protein 2, LOC647121, family with sequence similarity 19 (chemokine (C—C motif)-like) member A2, gamma-glutamyltransferase light chain 1 transcript variant A, LOC439949, LOC653157, neurotrophin 3, LOC649686, zinc finger protein 830 (ZNF830), glycerol kinase 5, leucine-rich repeat-containing G protein receptor 6 transcript variant 3, small nucleolar RNA C/D box 13, cDNA FLJ11554 fis clone HEMBA1003037, zinc finger protein 485; agents that specifically bind to at least one invariant control marker, a container for housing said agents; and instructions for use of the agents for determining an increase or decrease in the expression levels of said at least three biomarkers by comparing the expression levels of said at least three biomarkers to said at least one invariant control marker wherein an increase or decrease in the level of expression of said at least three biomarkers as compared to the at least one invariant control marker is indicative of a lower respiratory infection.

Some embodiments of the present invention relate to a kit for use in diagnosing a lower respiratory infection in a subject comprising polynucleotides that specifically bind to RNA transcripts of one or more biomarkers and of at least one invariant control marker.

Some embodiments of the present invention relate to a kit for use in diagnosing a lower respiratory infection in a subject comprising polynucleotides labeled with a detectable marker.

Some embodiments of the present invention relate to a kit for use in diagnosing a lower respiratory infection in a subject comprising polynucleotides that amplify polynucleotides encoding one or more biomarkers and at least one invariant control marker.

Some embodiments of the present invention relate to a kit for use in diagnosing a lower respiratory infection in a subject comprising instructions for calculating a biomarker infection score from an increase or decrease in the expression levels of one or more biomarkers and comparing said biomarker infection score to a control score.

Some embodiments of the present invention relate to a kit for use in diagnosing a lower respiratory infection in a subject comprising instructions for determining an increase or decrease in the expression levels of one or more biomarkers by using a multivariate prediction model to determine if a pattern of expression of said one or more biomarkers is indicative of a lower respiratory infection.

Some embodiments of the present invention relate to a kit for use in diagnosing a lower respiratory infection in a subject comprising agents that specifically bind to one or more biomarkers selected from the group consisting of bactericidal/permeability-increasing protein, myeloperoxidase, resistin, G antigen 12F, CD40 molecule TNF receptor superfamily member 5 transcript variant 2, and splicing factor 1 transcript variant 4.

Some embodiments of the present invention relate to a kit for use in diagnosing a lower respiratory infection in a subject comprising agents that specifically bind to defensin alpha-1, alkaline phosphatase liver isoform (ALPL), interleukin-8 receptor beta (IL8RB).

Some embodiments of the present invention relate to a kit for use in diagnosing a lower respiratory infection in a subject comprising agents that specifically bind to at least one invariant control marker selected from the group consisting of actin-beta (ACTB), Spi-B transcription factor, protein phosphatase 1 regulatory subunit 21 (PPP1R21, KLRAQ1), mitogen-activated protein kinase kinase kinase 7 (MAP3K7, TAK1), olfactory receptor family 51 subfamily member 1 (OR51M1), BCL2 antagonist/killer (BAK1), and adenosine deaminase, RNA-specific (ADAR1).

Some embodiments of the present invention relate to a kit for use in diagnosing a lower respiratory infection in a subject comprising reagents for fluorescently-labeled probes complementary to the one or more biomarkers, a ligase-based assay, reverse transcriptase and polymerase chain reaction, RNA sequencing or cDNA microarray.

Some embodiments of the present invention include a method of diagnosing a lower respiratory infection in a subject comprising: obtaining a biological sample from said subject; and contacting the biological sample from said subject with a kit for use in diagnosing a lower respiratory infection in a subject.

Some embodiments of the present invention include a method of treating a lower respiratory infection in a subject comprising: obtaining a biological sample from said subject; contacting the biological sample from said subject with a kit for use in diagnosing a lower respiratory infection in a subject; and treating the subject for a lower respiratory infection by administering antibiotics to said subject, administering antivirals to said subject, administering anti-inflammatories to said subject, or a combination thereof.

Definitions

To facilitate an understanding of the present invention, a number of terms and phrases are defined below.

As used herein, the singular forms "a", "an", and "the" include plural forms unless the context clearly dictates otherwise. Thus, for example, reference to "a binding agent" includes reference to more than one binding agent.

The terms "diagnostic" and "diagnosis" refer to identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

The terms "subject", "patient" or "individual" generally refer to a human, although the methods of the invention are not limited to humans, and should be useful in other mammals (e.g., cats, dogs, etc.).

"Sample" is used herein in its broadest sense. A sample may comprise a bodily fluid including blood, serum, plasma, tears, sputum, broncheolar lavage, aqueous and vitreous humor, spinal fluid, urine, and saliva; a soluble fraction of a cell or tissue preparation, or media in which cells were grown. Means of obtaining suitable biological samples are known to those of skill in the art.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, hybrid antibodies, fusion proteins comprising an antibody portion, and any other modified immunoglobulin molecule comprising an antigen recognition site so long as the antibodies exhibit the desired biological activity. An antibody may be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies may be naked or conjugated to other molecules such as toxins, radioisotopes, enzymes, fluorochromes, etc.

The term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

"Hybrid antibodies" are immunoglobulin molecules in which pairs of heavy and light chains from antibodies with different antigenic determinant regions are assembled together so that two different epitopes or two different antigens may be recognized and bound by the resulting tetramer.

"Isolated" in regard to cells, refers to a cell that is removed from its natural environment and that is isolated or separated, and is at least about 30%, 50%, 75%, and 90% free from other cells with which it is naturally present, but which lack the marker based on which the cells were isolated.

For use in the diagnostic and therapeutic applications described herein, kits are also within the scope of some embodiments of the current invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a biomarker of interest. Alternatively, the kit can comprise a mass spectrometry (MS) probe. The kit can also include containers containing nucleotide(s) for amplification or silencing of a target nucleic acid sequence, and/or a container comprising a reporter, such as a biotin-binding protein, e.g., avidin or streptavidin, bound to a detectable label, e.g., an enzymatic, florescent, or radioisotope label. The kit can include all or part of the amino acid sequence of the biomarker, or a nucleic acid molecule that encodes such amino acid sequences.

A kit according to an embodiment of the current invention may comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert that is included with the kit.

Polynucleotides may be prepared using any of a variety of techniques known in the art. The polynucleotide sequences selected as probes (and bind to the biomarkers of interest) should be sufficiently long and sufficiently unambiguous that false positives are minimized. The polynucleotide is preferably labeled such that it can be detected upon hybridization to DNA and/or RNA in the assay being screened. Methods of labeling are well known in the art, and include the use of radiolabels, such as 32P-labeled ATP, biotinylation, fluorescent groups or enzyme labeling. Hybridization conditions, including moderate stringency and high stringency, are well known in the art.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis. Alternatively, DNA and RNA molecules may be generated in vitro or in vivo. Certain portions may be used to prepare an encoded polypeptide.

Any polynucleotide may be further modified to increase stability in vivo and/or in vitro for improved activity and/or storage. Possible modifications include, but are not limited to, the addition of flanking sequences at the 5' and/or 3' ends; the use of phosphorothioate or 2' 0-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotides and/or antibodies specific to biomarkers of interest can be conjugated to detectable markers to a second molecule. Suitable detectable markers include, but are not limited to, a radioisotope, a fluorescent compound, a bioluminescent compound, chemiluminescent compound, a metal chelator or an enzyme. A second molecule for conjugation can be selected in accordance with the intended use. For example, for therapeutic use, the second molecule can be a toxin or therapeutic agent. Further, bi-specific antibodies specific for two or more biomarkers may be generated using methods generally known in the art. Homodimeric antibodies may also be generated by cross-linking techniques known in the art.

EXAMPLES

The following examples help explain some concepts of the current invention. However, the general concepts of the current invention are not limited to the particular examples.

Example 1: Blood Biomarkers for Respiratory Infections

The following factors are taken into consideration in this embodiment of the present invention:

1) Sample: In some embodiments, whole blood is the primary type of sample, in which the whole blood is drawn into a suitable preservative known to stabilize and protect the RNA. Blood drawn by venipuncture, in-dwelling catheter, or finger stick, are recognized and reliable methods of obtaining a blood sample from a human or other subject.

2) Time/Cost. Time is a major design driver. Prolonged analytical time a) delays treatment, b) requires revisit by the sick patient, and c) increases exposures to family and other patients. The use of RNA and/or cell-based systems could dramatically reduce time and costs because the volume of reagents in a microchamber can be extremely efficient and the time of quantitation can be reduced to hours or minutes, depending on the technology employed.

3) Sensitivity. In many infections, including LRI, and especially appendicitis (e.g. resulting from infection), sinus infections, and brain infections, the pathogen may never circulate at detectable levels in blood. In many cases, bacteria can form 'biofilms', which can line the appendix, lungs, or sinuses and cause extreme inflammation without ever circulating in blood. However, the presently claimed method takes advantage of the fact that the blood will contain immune cells that have passed close enough to become activated by pathogen-derived diffusible signals, such as endotoxin and butyrate.

4) Selectivity. A cell-based system can distinguish viral from bacterial infections because the cellular systems that respond to viruses and bacteria are quite different. Viral markers as well as bacterial markers can be used in embodiments of the invention. Clearly, the first question is really whether the person has an infection, versus an inflammatory reaction to allergens, a persistent inflammatory condition, such as bronchitis, asthma, or chronic obstructive pulmonary disease (COPD), which are treated very differently from an infection. By ruling out an infection, the doctor can decide whether antihistamines for allergy, or steroids for bronchitis are more appropriate.

Identification of Biomarkers in Blood

Using genomic-scale RNA transcript profiling, 79 RNA markers in blood were identified. Any of these (alone or in combination with other of the biomarkers) constitute a predictive biomarker of infection. These biomarkers are used in any of a variety of conventional test formats, such as measuring RNA level, protein level, or protein activity.

Methods: A total of >270 patients presenting to the GW Emergency Department were consented for a blood sample by venipuncture under an IRB-approved protocol. Their clinical course was unaffected by study procedures. Based on the final diagnosis, subsets of patients were analyzed by advanced genomic-scale RNA expression profiling of their blood using Illumina BeadChip Arrays (v12.4). Expression profiles from patients with acute appendicitis (APP), lower respiratory infection (LRI), or a presumably non-infectious control, abdominal hernia (HER), were compared to identify differentially expressed genes (DEG). The studies herein are focused on the LRI patients (n=5) compared to APP (n=9) and HER (n=4), in which APP and HER are pooled to form a Control group (Con).

Targets: The gene expression profiling reported herein revealed 79 transcripts (16 increased, 63 decreased) that were changed more than 3-fold at an uncorrected p value of <0.001 (Table 1). Furthermore, 11 of these transcripts were elevated more than 6-fold and 51 decreased in LRI by more than 6-fold, providing good signal/noise ratio for a biomarker. Published microarray analysis of whole blood RNA from chronic obstructive pulmonary disease (COPD) patients has identified some of the markers described herein. However, their levels were associated with the primary endpoint of ICU vs non-ICU status of the patient, and not specifically the presence of a respiratory infection (Almansa 2012). In embodiments of the present invention, markers that are specifically associated with respiratory infections are employed in order to detect infections in a patient without regard to ICU status, but rather as general guide to a physician in determining therapy. In some embodiments of the present invention, the previously identified markers are used in conjunction with one or more new markers that are identified herein.

Examples of LRI Biomarkers in Blood: (a Full List of the 79 Biomarkers is Found in Table 1 Below)

Transcripts elevated in LRI: Of the 79 transcripts, 16 transcripts were increased in LRI, and several of these transcripts have known proteins, some of which have been associated with the response to infection. However, the levels of these RNAs have not been shown to be diagnostic of infection. Exemplary markers that are used in embodiments of the invention include:

Bactericidal/permeability-increasing protein (BPI), increased >7-fold in LRI, is known to be elevated in patients with LRI (Lange 2013). Patients with severe sepsis show elevated plasma levels of BPI protein, defensin A1 (DEFA1) protein, and lactoferrin (LTF) protein (Berkestedt 2010). In some embodiments of the present invention, the previously identified markers are used in conjunction with one or more new markers that are identified herein.

Myeloperoxidase (MPO), increased >9-fold in LRI, is a neutrophil granule protein, which works with NADPH oxidase to convert H2O2 to hypochlorous acid (bleach), which is a potent microbiocidal agent. MPO generates bleach in high concentrations within the phagosome that engulfs bacteria into the neutrophil. While MPO mRNA is induced in LRI patients, secreted MPO protein in plasma is complicated due to specific neutralization of MPO in plasma by agents such as cerruloplasmin, which limits the utility a simple MPO activity test on plasma. Thus, cellular levels of MPO mRNA or protein are likely useful biomarkers for diagnostic tests.

Resistin (RETN), increased ~6-fold in LRI, is stored in neutrophil granules and released upon neutrophil activation, along with lactoferrin and CR3/CD11b (Bostrom 2009). Plasma levels of resistin, NGAL, and IL-8 distinguished uncomplicated sepsis from septic shock (Macdonald 2014). Resistin protein is elevated in septic patients, and released from neutrophils by streptococcal cell wall (Johansson 2009). Resistin RNA and protein are principally in neutrophils, and to a lesser degree monocytes. Resistin RNA expression is induced by lipopolysaccharide (LPS) in neutrophils and U937 (Kunnari AM 2009 19445973). However, RETN has not been previously shown to be a predictive marker of infection (e.g. in humans).

Defensins (DEFA1B, HNP-1, LOC653600) are a group of small peptides that are intrinsically involved in the host defense against pathogens. Typically contained within the azurophilic neutrophil granules, these proteins can directly attack bacteria, and potentially viruses, when they internalized within a host immune cell such as the neutrophil. The specific defensins identified in our microarray screen are multiple transcripts which derive from the DEFA1/3 locus in the genome at the location chr8:6,977,650-7,018,500 in the hg38 genome build. A variety of transcripts and proteins are made from this locus which are categorized as DEFA1 or DEFA3 depending on the usage of the included exons. For the purposes of the present invention, any transcripts derived from this locus may be suitable for diagnosis, and the DEFA1 version of the mRNA is used for demonstration of the utility, but is not limiting in practice of the invention.

Transcripts which are Decreased in LRI:

GAGE12F transcript is decreased ~17-fold in patients with LRI. No biological or physiological function has been described for GAGE12F, and it has not been shown previously to be a biomarker for infection.

CD40 transcript is >12-fold decreased in patients with LRI. CD40 is a well-known protein that is grouped into the Tumor Necrosis Factor (TNF) receptor superfamily. However, decreased mRNA levels of CD40 have not been shown previously to be correlated with LRI or any other infection.

Splicing factor 1 (SF1) transcript variant 4, is decreased >12-fold in patients with LRI. SF1 is a well-known protein involved in regulating the splicing of certain transcripts in diverse settings. However, decreased mRNA levels of SF1

(e.g. of transcript variant 4) have not been shown previously to be correlated with bacterial or viral infection, e.g. of humans.

Invariant Transcripts to be Used as Controls:

There are numerous transcripts that do not change between groups, and these can be used as 'normalizing' genes (controls) to compensate for handling and technical errors that might affect a particular sample. Examples of invariant gene transcripts include KLRAQ1, MAP3K7, OR51M1, BAK1, and ADAR1, although this list is not meant to be exclusive of other invariant transcripts.

Calculation of the Infection Score:

The normalized signal values (SV) of 3 increased transcripts (RSTN, BPI, MPO) are added together and divided by the sum of the 3 invariant SVs. Likewise, the 3 decreased transcripts (GAGE12F, CD40, SF1) are added together and divided by the sum of 3 invariant transcripts. In one embodiment, +12.5 fold is added to [−14 fold] to create a score of 26.5, there would thus be a normal range and escalating probabilities of infection.

TABLE 1

Differentially expressed gene transcripts relevant to lower respiratory infection.

| ProbeID | p-value | FC (abs) | Con | LRI | DEFINITION |
| --- | --- | --- | --- | --- | --- |
| 770400 | 3.61E−04 | 17.78 | UP | 0.43 | 4.58 Neutrophil defensin 1 precursor (HNP-1) (HP-1) (HP1) (Defensin, alpha 1) (LOC653600), mRNA. |
| 7150170 | 8.79E−04 | 15.79 | UP | 2.62 | 6.60 defensin, alpha 1B (DEFA1B), mRNA. |
| 6040689 | 7.25E−04 | 9.32 | UP | −5.04 | −1.82 SHC (Src homology 2 domain containing) transforming protein 3 (SHC3), mRNA. |
| 3520601 | 8.41E−05 | 9.29 | UP | −0.31 | 2.91 myeloperoxidase (MPO), nuclear gene encoding mitochondrial protein, mRNA. |
| 4390398 | 2.40E−04 | 8.80 | UP | 3.04 | 6.18 lipocalin 2 (LCN2), mRNA. |
| 1500735 | 8.77E−04 | 7.95 | UP | 0.08 | 3.07 cathepsin G (CTSG), mRNA. |
| 4200746 | 4.41E−04 | 7.48 | UP | 0.20 | 3.11 bactericidal/permeability-increasing protein (BPI), mRNA. |
| 5550367 | 7.76E−04 | 6.98 | UP | 0.58 | 3.38 lactotransferrin (LTF), mRNA. |
| 2340156 | 2.69E−04 | 6.85 | UP | −6.14 | −3.37 solute carrier family 22 (organic cation transporter), member 2 (SLC22A2), mRNA. |
| 5310142 | 3.33E−04 | 6.60 | UP | −1.66 | 1.06 methyltransferase like 7B (METTL7B), mRNA. |
| 4610129 | 9.27E−04 | 6.24 | UP | 0.86 | 3.50 resistin (RETN), mRNA. |
| 5360427 | 6.81E−04 | 5.52 | UP | −5.55 | −3.08 zinc finger protein 90 (HTF9) (ZNF90), mRNA. |
| 6860347 | 8.48E−05 | 3.93 | UP | 4.82 | 6.80 family with sequence similarity 46, member C (FAM46C), mRNA. |
| 270152 | 2.80E−04 | 3.38 | UP | 1.57 | 3.33 solute carrier family 7 (cationic amino acid transporter, y+ system), member 5 (SLC7A5), mRNA. |
| 5270338 | 8.32E−04 | 3.19 | UP | −1.00 | 0.68 aminolevulinate, delta-, synthase 2 (ALAS2), nuclear gene encoding mitochondrial protein, transcript variant 3, mRNA. |
| 6840301 | 8.42E−04 | 3.13 | UP | −0.40 | 1.25 5'-nucleotidase domain containing 2 (NT5DC2), mRNA. |
| 4060551 | 5.30E−07 | 19.07 | Down | −2.12 | −6.37 PREDICTED: similar to hCG1774990 (LOC646021), mRNA. |
| 6620326 | 1.00E−04 | 17.03 | Down | −2.28 | −6.37 G antigen 12F (GAGE12F), mRNA. |
| 990170 | 1.14E−05 | 15.29 | Down | −1.09 | −5.03 PREDICTED: misc_RNA (LOC100133075), miscRNA. |
| 4880280 | 4.09E−05 | 14.11 | Down | −2.55 | −6.37 PREDICTED: hypothetical protein FLJ23865 (FLJ23865), mRNA. |
| 430162 | 4.06E−04 | 13.26 | Down | −2.64 | −6.37 RST17329 Athersys RAGE Library cDNA, mRNA sequence |
| 1240382 | 1.11E−04 | 13.03 | Down | −1.56 | −5.26 PREDICTED: hypothetical protein LOC339047, transcript variant 74 (LOC339047), mRNA. |
| 3370138 | 1.25E−04 | 12.53 | Down | −0.82 | −4.47 CD40 molecule, TNF receptor superfamily member 5 (CD40), transcript variant 2, mRNA. |
| 3610743 | 4.35E−04 | 12.30 | Down | 0.16 | −3.46 splicing factor 1 (SF1), transcript variant 4, mRNA. |
| 5340224 | 5.34E−05 | 11.75 | Down | −2.81 | −6.37 synaptophysin-like 1 (SYPL1), transcript variant 1, mRNA. |
| 4280678 | 3.15E−04 | 11.25 | Down | −2.24 | −5.73 selenoprotein P, plasma, 1 (SEPP1), transcript variant 1, mRNA. |
| 6350093 | 3.87E−04 | 11.08 | Down | −1.57 | −5.04 mRNA; cDNA DKFZp779F0411 (from clone DKFZp779F0411) |
| 5390717 | 5.01E−05 | 10.87 | Down | −1.40 | −4.85 PREDICTED: similar to hCG1730248 (LOC643037), mRNA. |
| 6380239 | 7.33E−04 | 10.82 | Down | −2.73 | −6.17 SH3-domain GRB2-like (endophilin) interacting protein 1 (SGIP1), mRNA. |
| 5860484 | 4.55E−05 | 10.69 | Down | −1.65 | −5.07 microRNA 940 (MIR940), microRNA. |

TABLE 1-continued

Differentially expressed gene transcripts relevant to lower respiratory infection.

| ProbeID | p-value | FC (abs) | Con | LRI | DEFINITION |
|---|---|---|---|---|---|
| 6580619 | 4.20E-04 | 10.68 | Down | -2.95 | -6.37 PR domain containing 12 (PRDM12), mRNA. |
| 5810113 | 8.74E-04 | 10.59 | Down | -2.76 | -6.17 oo20c08.x1 Soares_NSF_F8_9W_OT_PA_P_S1 cDNA clone IMAGE: 1566734 3, mRNA sequence |
| 4390528 | 4.16E-04 | 10.26 | | -1.83 | -5.19 PREDICTED: misc_RNA (LOC100128771), miscRNA. |
| 5890598 | 3.41E-05 | 10.19 | Down | -2.18 | -5.53 PREDICTED: similar to ring finger protein 18 (LOC732387), mRNA. |
| 6770068 | 2.91E-04 | 9.77 | Down | -2.88 | -6.17 PREDICTED: region containing hypothetical protein LOC283970; similar to nuclear pore complex interacting protein, transcript variant 2 (LOC643943), mRNA. |
| 7570431 | 1.47E-04 | 9.50 | Down | -1.37 | -4.62 PREDICTED: hypothetical protein LOC100129705 (LOC100129705), mRNA. |
| 2650128 | 9.05E-05 | 9.40 | Down | -2.47 | -5.70 PREDICTED: misc_RNA (LOC728522), miscRNA. |
| 6400403 | 2.12E-04 | 9.27 | Down | -2.36 | -5.57 regulator of G-protein signaling 20 (RGS20), transcript variant 1, mRNA. |
| 2190100 | 9.82E-04 | 9.11 | Down | -1.83 | -5.02 kelch domain containing 1 (KLHDC1), mRNA. |
| 6650192 | 7.74E-04 | 9.01 | Down | -2.02 | -5.19 PREDICTED: misc_RNA (LOC100134669), miscRNA. |
| 2450300 | 6.13E-04 | 8.98 | Down | -3.20 | -6.37 tripartite motif-containing 34 (TRIM34), transcript variant 2, mRNA. |
| 5050072 | 3.85E-05 | 8.96 | Down | -1.43 | -4.59 ribosomal protein L10-like (RPL10L), mRNA. |
| 4050482 | 7.43E-04 | 8.70 | Down | -2.47 | -5.59 PREDICTED: similar to Fanconi anemia complementation groDOWN D2 protein (LOC100129929), mRNA. |
| 770110 | 5.48E-04 | 8.61 | Down | -2.12 | -5.23 PREDICTED: similar to UDP-Gal: betaGlcNAc beta 1,3-galactosyltransferase, polypeptide 4 (LOC402377), mRNA. |
| 3060520 | 7.72E-04 | 8.60 | Down | -0.20 | -3.30 PREDICTED: similar to MHC class II antigen (LOC642073), mRNA. |
| 1820474 | 5.80E-04 | 8.36 | Down | -2.47 | -5.53 zinc finger protein 461 (ZNF461), mRNA. |
| 5570021 | 4.57E-04 | 8.31 | Down | -2.60 | -5.65 creatine kinase, mitochondrial 1B (CKMT1B), nuclear gene encoding mitochondrial protein, mRNA. |
| 1010072 | 3.14E-04 | 8.16 | Down | -1.71 | -4.74 yy43f04.sl Soares melanocyte 2NbHM cDNA clone IMAGE: 274015 3, mRNA sequence |
| 2100162 | 9.49E-04 | 8.11 | Down | -2.06 | -5.08 KIAA1045 (KIAA1045), mRNA. |
| 5810682 | 1.58E-04 | 8.09 | Down | -1.87 | -4.89 PREDICTED: misc_RNA (ZNF788), miscRNA. |
| 6370228 | 6.94E-05 | 8.04 | Down | 0.09 | -2.92 primary neuroblastoma cDNA, clone: Nbla10527, full insert sequence |
| 6550484 | 3.42E-04 | 8.03 | Down | -1.97 | -4.97 processing of precursor 5, ribonuclease P/MRP subunit (S. cerevisiae) (POP5), transcript variant 2, mRNA. |
| 2190358 | 2.25E-04 | 7.86 | Down | -1.94 | -4.92 myelin transcription factor 1-like (MYT1L), mRNA. |
| 4590037 | 1.10E-04 | 7.81 | Down | -1.39 | -4.36 neuroblastoma breakpoint family, member 7 (NBPF7), mRNA. |
| 2100356 | 6.42E-04 | 7.75 | Down | -1.70 | -4.65 phospholipase C-like 1 (PLCL1), mRNA. |
| 6770452 | 2.13E-04 | 7.52 | Down | -1.89 | -4.80 PREDICTED: similar to hCG1809904 (LOC391761), mRNA. |
| 5810768 | 1.78E-04 | 7.51 | Down | -1.36 | -4.27 PREDICTED: hypothetical LOC646498 (LOC646498), mRNA. |
| 6380364 | 4.53E-04 | 7.46 | Down | -1.27 | -4.17 solute carrier family 7 (cationic amino acid transporter, y+ system), member 6 (SLC7A6), transcript variant 2, mRNA. |
| 3940750 | 1.13E-04 | 7.42 | Down | -1.91 | -4.81 PREDICTED: similar to hCG2024106, transcript variant 1 (LOC100134648), mRNA. |
| 7380161 | 2.21E-04 | 7.27 | Down | -3.11 | -5.97 PREDICTED: neuroblastoma breakpoint family, member 1, transcript variant 16 (NBPF1), mRNA. |
| 4220376 | 2.06E-04 | 7.23 | Down | -2.11 | -4.97 absent in melanoma 1-like (AIM1L), mRNA. |

TABLE 1-continued

Differentially expressed gene transcripts relevant to lower respiratory infection.

| ProbeID | p-value | FC (abs) | Con | LRI | DEFINITION |
|---|---|---|---|---|---|
| 5270603 | 4.32E−04 | 7.21 | Down | −1.50 −4.35 | EPS8-like 2 (EPS8L2), mRNA. XM_943956 XM_943960 XM_943963 XM_943966 |
| 5050707 | 1.55E−04 | 7.19 | Down | −1.09 −3.93 | angiopoietin-like 6 (ANGPTL6), mRNA. |
| 4850110 | 4.74E−04 | 6.73 | Down | −2.09 −4.84 | PREDICTED: hypothetical protein LOC645743 (LOC645743), mRNA. |
| 5870091 | 6.14E−04 | 6.59 | Down | −2.03 −4.75 | V-set and transmembrane domain containing 2A (VSTM2A), mRNA. |
| 460504 | 2.31E−04 | 6.50 | Down | −2.14 −4.84 | chemokine binding protein 2 (CCBP2), mRNA. |
| 6350445 | 6.13E−04 | 6.20 | Down | −1.44 −4.07 | PREDICTED: similar to embigin homolog (LOC647121), mRNA. |
| 3520114 | 9.96E−04 | 5.71 | Down | −1.32 −3.84 | family with sequence similarity 19 (chemokine (C-C motif)-like), member A2 (FAM19A2), mRNA. |
| 60735 | 5.14E−04 | 5.55 | Down | −2.64 −5.12 | gamma-glutamyltransferase light chain 1 (GGTLC1), transcript variant A, mRNA. |
| 4560088 | 6.52E−04 | 5.54 | Down | 1.03 −1.44 | PREDICTED: hypothetical gene sDOWNported by AY007155 (LOC439949), mRNA. |
| 4050132 | 6.18E−04 | 5.49 | Down | 0.55 −1.91 | PREDICTED: similar to Iduronate 2-sulfatase precursor (Alpha-L-iduronate sulfate sulfatase) (Idursulfase) (LOC653157), mRNA. |
| 21540441 | 6.28E−04 | 4.92 | Down | −1.75 −4.05 | neurotrophin 3 (NTF3), mRNA. |
| 6020553 | 8.44E−04 | 4.67 | Down | −1.17 −3.39 | PREDICTED: similar to Neuronal acetylcholine receptor protein, beta-4 subunit precursor (LOC649686), mRNA. |
| 2320593 | 3.73E−04 | 4.23 | Down | −0.61 −2.69 | zinc finger protein 830 (ZNF830), mRNA. |
| 6180543 | 6.30E−04 | 4.04 | Down | −0.51 −2.53 | glycerol kinase 5 (putative) (GK5), mRNA. |
| 3610154 | 1.53E−04 | 4.00 | Down | −0.69 −2.69 | leucine-rich repeat-containing G protein-coDOWNled receptor 6 (LGR6), transcript variant 3, mRNA. |
| 7210035 | 8.97E−04 | 3.60 | Down | 1.05 −0.80 | small nucleolar RNA, C/D box 13 (SNORD13), small nucleolar RNA. |
| 5260021 | 1.18E−04 | 3.44 | Down | −0.66 −2.44 | cDNA FLJ11554 fis, clone HEMBA1003037 |
| 670279 | 1.34E−05 | 3.38 | Down | −0.49 −2.25 | zinc finger protein 485 (ZNF485), mRNA. |

Table Headers:
PROBE_ID refers to the specific cDNA probe sequences used to detect the RNA transcript as described by the manufacturer of the Illumina Bead Chip version 12.4.
P value refers to the t-test probability that the two groups of samples are actually derived from the same distribution of variance. A smaller value indicates a greater chance that the expression levels in two groups are significantly different in magnitude.
FC (abs) refers to 'fold change' in absolute terms, i.e. corrected for the log 2 expression levels in the subsequent columns, which is the relative change in expression between groups.
Con refers to the control group, and LRI refers to the lower respiratory infection group, where the values are normalized expression values expressed on log 2 scale. Thus, if Con is 1 and LRI is 3, then the difference is $2^2=4$ fold change (FC)
DEFINITION is the formal name of the transcript as described in Genbank or Refseq, as related by the manufacturer's library file for the microarray.
SYMBOL refers to the official gene symbol abbreviation, when available.
The Genbank or Refseq numbers were obtained from NIH databases and the Illumina library file for the microarray. A given transcript can have multiple Genbank identifiers reflecting different studies that independently observed the sequence is a specific context.
Additional information on the biomarkers from Table 1, including the gene symbol and synonyms appear in Table 2 below.

TABLE 2

Definitions, gene symbols and synonym of biomarkers from Table 1.

| DEFINITION (SYMBOL) | SYNONYMS |
|---|---|
| *Homo sapiens* absent in melanoma 1-like (AIM1L), mRNA. | FLJ10040; DKFZp434L1713; FLJ38020 |
| *Homo sapiens* aminolevulinate, delta-, synthase 2 (ALAS2), nuclear gene encoding mitochondrial protein, transcript variant 3, mRNA, | ASB; XLSA; ANH1 |

TABLE 2-continued

Definitions, gene symbols and synonym of biomarkers from Table 1.

| DEFINITION (SYMBOL) | SYNONYMS |
|---|---|
| *Homo sapiens* angiopoietin-like 6 (ANGPTL6), mRNA. | AGF; ARP5 |
| *Homo sapiens* bactericidal/permeability-increasing protein (BPI), mRNA. | |
| *Homo sapiens* chemokine binding protein 2 (CCBP2), mRNA. | D6; CCR9; MGC138256; MGC126678; CCR10; hD6; CMKBR9 |
| *Homo sapiens* CD40 molecule, TNF receptor superfamily member 5 (CD40), transcript variant 2, mRNA. | CDW40; TNFRSF5; p50; MGC9013; Bp50 |
| *Homo sapiens* creatine kinase, mitochondrial 1B (CKMT1B), nuclear gene encoding mitochondrial protein, mRNA. | UMTCK; CKMT1; CKMT |
| *Homo sapiens* cathepsin G (CTSG), mRNA. | M16117 |
| *Homo sapiens* defensin, alpha 1B (DEFA1B), mRNA. | |
| *Homo sapiens* EPS8-like 2 (EPS8L2), mRNA. XM_943956 XM_943960 XM_943963 XM_943966 | FLJ16738; EPS8R2; FLJ21935; MGC3088; FLJ22171; MGC126530 |
| *Homo sapiens* family with sequence similarity 19 (chemokine (C-C motif)-like), member A2 (FAM19A2), mRNA. | DKFZp781P0552; TAFA-2 MGC42403; DKFZp761E1217; TAFA2 |
| *Homo sapiens* family with sequence similarity 46 member C (FAM46C), mRNA. | FLJ20202 |
| PREDICTED: *Homo sapiens* hypothetical protein FLJ23865 (FLJ23865), MRNA. | |
| *Homo sapiens* G antigen 12F (GAGE12F), mRNA. | |
| *Homo sapiens* gamma-glutamyltransferase light chain 1 (GGTLC1), transcript variant A, mRNA. | dJ831C21.2: MGC50550 |
| *Homo sapiens* glycerol kinase 5 (Putative) (GK5), mRNA. | MGC40579; FLJ45739; FLJ33582 |
| RST17329 Athersys RAGE Library *Homo sapiens* cDNA, mRNA sequence | |
| *Homo sapiens* cDNA FLJ11554 fis, clone HEMBA1003037 | |
| yy43f04.s1 Soares melanocyte 2NbHM *Homo sapiens* cDNA clone IMAGE: 274015 3, mRNA sequence | |
| *Homo sapiens* primary neuroblastoma cDNA, clone: Nbla10527, Full insert sequence | |
| pleckstrin homology domain interacting protein | |
| oo20c08.x1 Soares_NSF_F8_9W_OT_PA_P_S1 *Homo sapiens* cDNA clone IMAGE: 1566734 3, mRNA sequence | |
| *Homo sapiens* KIAA1045 (KIAA1045), mRNA. | RP11-392A14.4; DKFZp434I2112 |
| *Homo sapiens* kelch domain containing 1 (KLHDC1), mRNA. | MST025; MGC126644; MGC126646 |
| *Homo sapiens* lipocalin 2 (LCN2), mRNA. | NGAL |
| *Homo sapiens* leucine-rich repeat-containing G protein-coupled receptor 6 (LGR6), transcript variant 3, mRNA. | VTS20631; FLJ14471; GPCR |
| PREDICTED: *Homo sapiens* misc_RNA (LOC100128771), miscRNA, | |
| PREDICTED: *Homo sapiens* hypothetical protein LOC100129705 (LOC100129705), mRNA. | |
| PREDICTED: *Homo sapiens* similar to Fanconi anemia complementation group D2 protein (LOC100129929), mRNA. | |
| PREDICTED: *Homo sapiens* misc_RNA (LOC100133075), miscRNA. | |
| PREDICTED: *Homo sapiens* similar to hCG2024106, transcript variant 1 (LOC100134648), mRNA. | |
| PREDICTED: *Homo sapiens* misc_RNA (LOC100134669), miscRNA, | |
| PREDICTED: *Homo sapiens* hypothetical protein LOC339047, transcript variant 74 (LOC339047), mRNA. | |
| PREDICTED: *Homo sapiens* similar to hCG1809904 (LOC391761), mRNA. | |
| PREDICTED: *Homo sapiens* similar to UDP-Gal:betaGlcNAc beta 1,3-galactosyltransferase, polypeptide 4 (LOC402377), mRNA. | |
| PREDICTED: *Homo sapiens* hypothetical one supported by AY007155 (LOC439949), mRNA, | |
| PREDICTED: *Homo sapiens* similar MHC class II antigen (LOC642073), mRNA. | |
| PREDICTED: *Homo sapiens* similar to hCG1730248 (LOC643037), mRNA. | |
| PREDICTED: *Homo sapiens* region containing hypothetical protein LOC283970; similar to nuclear pore complex interacting protein, transcript variant 2 (LOC643943), mRNA. | |
| PREDICTED: *Homo sapiens* hypothetical protein LOC645743 (LOC645743), mRNA. | |
| PREDICTED: *Homo sapiens* similar to hCG1774990 (LOC646021), mRNA. | |

TABLE 2-continued

Definitions, gene symbols and synonym of biomarkers from Table 1.

| DEFINITION (SYMBOL) | SYNONYMS |
|---|---|
| PREDICTED: *Homo sapiens* hypothetical LOC646498 (LOC646498), mRNA. | |
| PREDICTED: *Homo sapiens* similar to embigin homolog (LOC647121), mRNA. | |
| PREDICTED: *Homo sapiens* similar to Neuronal acetylcholine receptor protein, beta-4 subunit precursor (LOC649686), mRNA. | |
| PREDICTED: *Homo sapiens* similar to Iduronate 2-sulfatase precursor (Alpha-1,-iduronate sulfate sulfatase) (Idursulfase) (LOC653157), mRNA. | |
| PREDICTED: *Homo sapiens* similar to Neutrophil defensin 1 precursor (HNP-1) (HP-1) (HPI) (Defensin alpha 1) (LOC653600), mRNA. | |
| PREDICTED: *Homo sapiens* misc_RNA (LOC728522), miscRNA. | |
| PREDICTED: *Homo sapiens* similar to ring finger protein 18 (LOC732387), mRNA. | |
| *Homo sapiens* lactotransferrin (LTF), mRNA. | HLF2; GIG12 |
| *Homo sapiens* methyltransferase like 7B (METTL7B), mRNA. | MGC17301 |
| *Homo sapiens* microRNA 940 (MTR940), microRNA. | |
| *Homo sapiens* myeloperoxidase (MPO), nuclear gene encoding mitochondrial protein, mRNA. | |
| *Homo sapiens* myelin transcription factor 1-like (MYT1L), mRNA. | |
| PREDICTED: *Homo sapiens* neuroblastoma breakpoint family, member 1, transcript variant 16 (NBPF1), mRNA. | |
| *Homo sapiens* neuroblastoma breakpoint family, member 7 (NBPF7), mRNA. | |
| *Homo sapiens* 5'-nucleotidase domain containing 2 (NT5DC2), mRNA. | FLJ12442 |
| *Homo sapiens* neurotrophin 3 (NTF3), mRNA. | HDNF; NGF-2; NT3; NGF2; MGC129711 |
| *Homo sapiens* phospholipase C-like 1 (PLCL1), mRNA. | MGC138190; PLDL1; PLCE; PLCL; PLC-L; MGC126580 |
| *Homo sapiens* processing of precursor 5, ribonuclease P/MRP subunit (*S. cerevisiae*) (POP5), transcript variant 2, mRNA. | HSPC004; RPP20; RPP2 |
| *Homo sapiens* PR domain containing 12 (PRDM12), mRNA. | PFM9 |
| *Homo sapiens* resistin (RETN), mRNA. | XCP1; MGC126603; RSTN; RETN1; MGC126609; FIZZ3; ADSF |
| *Homo sapiens* regulator of G-protein signaling 20 (RGS20), transcript variant 1, mRNA. | ZGAP1; RGSZ1 |
| *Homo sapiens* ribosomal protein L10-like (RPL10L), mRNA. | FLJ27353 |
| *Homo sapiens* selenoprotein P, plasma, 1 (SEPP1), transcript variant 1, mRNA. | SeP; SELP |
| *Homo sapiens* splicing factor 1 (SF1), transcript variant 4, mRNA. | D11S636; ZNF162; ZFM1 |
| *Homo sapiens* SH3-domain GRB2-like (endophilin) interacting protein 1 (SGIP1), mRNA. | FLJ43054; DKFZp761D221; FLJ33378; DKFZp686A16142 |
| *Homo sapiens* SHC (Src homology 2 domain containing) transforming protein 3 (SHC3), mRNA. | SHCC; N-Shc; NSHC |
| *Homo sapiens* solute carrier family 22 (organic cation transporter), member 2 (SLC22A2), mRNA. | OCT2; MGC32628 |
| *Homo sapiens* solute carrier family 7 (cationic amino acid transporter, y+ system), member 5 (SLC7A5), mRNA. | MPE16; CD98; 4F2LC; hLAT1; D16S469E; LAT1; E16 |
| *Homo sapiens* solute carrier family 7 (cationic amino acid transporter, y+ system), member 6 (SLC7A6), transcript variant 2, mRNA. | DKFZp686K15246; KIAA0245; LAT3; LAT-2; y+LAT-2 |
| *Homo sapiens* small nucleolar RNA, C/D box 13 (SNORD13), small nucleolar RNA. | U13 |
| *Homo sapiens* synaptophysin-like 1 (SYPL1), transcript variant 1, mRNA. | H-SP1; SYPL |
| *Homo sapiens* tripartite motif-containing 34 (TRIM34), transcript variant 2, mRNA. | RNF21; IFP1 |
| *Homo sapiens* V-set and transmembrane domain containing 2A (VSTM2A), mRNA. | MGC33530; VSTM2 |
| *Homo sapiens* zinc finger protein 461 (ZNF461), mRNA. | GIOT-1; ZNF461; GIOT1; MGC33911 |
| *Homo sapiens* zinc finger protein 485 (ZNF485), mRNA. | |
| PREDICTED: *Homo sapiens* misc_RNA (ZNF788), miscRNA. | |
| *Homo sapiens* zinc finger protein 830 (ZNF830), mRNA. | MGC20398 |
| PREDICTED: *Homo sapiens* zinc finger protein 90 (HTF9) (ZNE90), mRNA, | |
| *Homo sapiens* alkaline phosphatase, liver/bone/kidney (ALPL), transcript variant 1, mRNA. | TNSALP; HOPS; FLJ40094; AP-TNAP; TNAP; MGC161443 |

TABLE 2-continued

Definitions, gene symbols and synonym of biomarkers from Table 1.

| DEFINITION (SYMBOL) | SYNONYMS |
|---|---|
| *Homo sapiens* interleukin 8 receptor, beta (IL8RB), mRNA. | CD182; CMKAR2; IL8RA; IL8R2; CXCR2; CDw128b |

Table Headers:
SYNONYMS are other recognized names for the gene or transcript.

GenBank and RefSEQ IDs for Each of the Genes from Tables 1 and 2 Appear Below:

*Homo sapiens* absent in melanoma 1-like (AIM1L), mRNA: FLJ10040; DKFZp434L1713; FLJ38020. GenBank/RefSeq IDs:

| AK000902 | NM_001039775 | AL451139 | CD628848 |
|---|---|---|---|
| AK095339 | CH471059 | BC136870 | DR004727 |
| DA439029 | AL137264. | | |

*Homo sapiens* aminolevulinate, delta-, synthase 2 (ALAS2), nuclear gene encoding mitochondrial protein transcript variant 3, mRNA:

| AY53084 | BP284609 | BM677888 | AK291589 |
|---|---|---|---|
| AY532085 | AY532086 | AY532087 | AY532088 |
| AY532089 | NM_001037967 | CR609889 | NM_001037968 |
| NM_000032 | CR615092 | AY532102 | AY532101 |
| Z83821 | AY532100 | CH471154 | AK313118 |
| AY532109 | AY532108 | AY532107 | AY532081 |
| AY532106 | AY532080 | AY532105 | AY532083 |
| AY532104 | AY532082 | AY532103 | AY532097 |
| AY532098 | AK290565 | AY532095 | AY532096 |
| CR593743 | X56352 | AY532099 | AY190322 |
| CR613185 | AY532094 | AY532093 | CR626361 |
| AY532092 | AY532091 | X60364 | CR591435 |
| AA778169 | AY532069 | CR606333 | AL020991 |
| CR620984 | BP233279 | CR606670 | AY532079 |
| AY532078 | CR608649 | AY532077 | AF068624 |
| AY532076 | AY532075 | AY532074 | AY532073 |
| BC030230 | AY532071 | AY532072 | AY532070 |
| BQ182291 | AF130113 | | |

*Homo sapiens* angiopoietin-like 6 (ANGPTL6), mRNA:

| CR591845 | CH471106 | AY358276 | AB054064 | BC142632 |
|---|---|---|---|---|
| NM_031917 | CR621970 | CR617920 | AC020931 | AF230330. |

*Homo sapiens* bactericidal/permeability-increasing protein (BPI), mRNA:

| CH471077 | J04739 | BP306215 | CQ800679 | Y14219 |
|---|---|---|---|---|
| Y14217 | BC032230 | Y14218 | AL583962 | Y14215 |
| Y14216 | AK296568 | AL359555 | AF322588 | Y14220 |
| AK315328 | A1436120 | Y14221 | Y14222 | Y14223 |
| AL499625 | Y14228 | Y14229 | Y14224 | Y14225 |
| NM_001725 | Y14226 | Y14227 | AL391692 | DQ414688 |
| BC040955. | | | | |

*Homo sapiens* chemokine binding protein 2 (CCBP2), mRNA:

| BC020558 | U94888 | BT006800 | CH471055 | AK313561 |
|---|---|---|---|---|
| DQ229109 | AC099329 | DA853159 | AY262687 | BC008816 |

| BC018716 | EU832737 | AF481959 | BC011588 | BC101629 |
|---|---|---|---|---|
| Y12815 | BC112045 | BE901130 | NM_001296 | CR610139 |
| BC011631. | | | | |

*Homo sapiens* CD40 molecule, TNF receptor superfamily member 5 (CD40), transcript variant 2, mRNA:

| CH471077 | NM_152854 | CS07717 | AK222896 | BC012419 |
|---|---|---|---|---|
| AB209660 | DQ871604 | AY225405 | BM761221 | CR605787 |
| AL035662 | EF064754 | CS103051 | DQ891804 | BC064518 |
| CR619622 | CS103053 | NM_001250 | CS097719 | CS097320 |
| AY504960 | AJ300189 | DQ894988 | BT019901 | X60592 |
| CS095651 | CS097318 | CR608994 | CS095653. | |

*Homo sapiens* creatine kinase, mitochondrial 1B (CKMT1B), nuclear gene encoding mitochondrial protein, mRNA:

| BC121002 | BC121001 | DQ893385 | BC108652 |
|---|---|---|---|
| AK294908 | AK293685 | AC011330 | CR618017 |
| AK293790 | AK293961 | NM_001015001 | AK316319 |
| AK316124 | DQ896705 | BC001926 | CR605038 |
| AK294735 | BU674851 | AK094322 | AK223365 |
| BM923431 | J04469 | AK296271 | AK294063 |
| AK296472 | NM_020990 | CR599868 | AK295776 |
| AK316052 | CR616544 | CR597545 | BT006628 |
| BI118196 | AK293939 | AK308770 | CR599511 |
| BC006467. | | | |

*Homo sapiens* cathepsin G (CTSG), mRNA:

| DQ893067 | CR456807 | BC014460 | NM_001911 | CR541704 |
|---|---|---|---|---|
| AK225914 | DQ896320 | AL136018 | AI272833 | J04990 |
| CH471078. | | | | |

*Homo sapiens* defensin, alpha 1B (DEFA1B), mRNA:

| AX405718 | L12690 | NM_004084 | AF238378 | AF200455 |
|---|---|---|---|---|
| BC069423 | X52053 | AF233439 | M26602 | BC093791 |
| DQ896798 | DQ890546 | DQ890545 | NM_001042500 | BC112188 |
| M21130. | | | | |

*Homo sapiens* EPS8-like 2 (EPS8L2), mRNA. XM_943956 XM_943960 XM_943963 XM_943966:

| BC101481 | BC080636 | AK025824 | AK094539 | AK122903 |
|---|---|---|---|---|
| AK294041 | BC093878 | AK222903 | AK225311 | AK122984 |
| AK025588 | NM_022772 | BC002474 | BC143242 | AF318331 |
| AP006621 | AY074929 | CH471158 | AK027765. | |

*Homo sapiens* family with sequence similarity 19 (chemokine (C—C motif)-like), member A2 (FAM19A2), mRNA:

| | | | | |
|---|---|---|---|---|
| AL834160 | AC078872 | BC028403 | CR749367 | AC078789 |
| CH471054 | AC020647 | AW161831 | NM_178539 | AY325115 |
| AC137053 | BC050347 | BC040286 | AK123580 | AC130414. |

*Homo sapiens* family with sequence similarity 46, member C (FAM46C), mRNA:

| | | | | |
|---|---|---|---|---|
| BC036516 | AL046016 | NM_017709 | AK091327 | CH471122 |
| BC131726 | AL365331 | AK000209 | CD300120. | |

PREDICTED: *Homo sapiens* hypothetical protein FLJ23865 (FLJ23865), mRNA: AK074445.

*Homo sapiens* G antigen 12F (GAGE12F), mRNA: NC000023.10.

*Homo sapiens* gamma-glutamyltransferase light chain 1 (GGTLC1), transcript variant A, mRNA:

| | | | | |
|---|---|---|---|---|
| NM_178311 | NM_178312 | CH471133 | BC040904 | L20491 |
| L20492 | AL133466. | | | |

*Homo sapiens* glycerol kinase 5 (putative) (GK5), mRNA:

| | | | | |
|---|---|---|---|---|
| DQ894800 | BX648681 | BC032470 | BX648359 | CH471052 |
| NM_001039547 | AC108679 | AK090901 | BU628781 | CR598125 |
| AK310761 | AK313792 | DQ891607 | AK130469 | DR000158 |
| AK127641. | | | | |

RST17329 Athersys RAGE Library *Homo sapiens* cDNA, mRNA sequence: Hs.134230.

*Homo sapiens* cDNA FLJ11554 fis, clone HEMBA1003037: AK021616.

yy43f04.s1 Soares melanocyte 2NbHM *Homo sapiens* cDNA clone IMAGE:274015 3, mRNA sequence: BC000393.

*Homo sapiens* primary neuroblastoma cDNA, clone:N-bla10527, full insert sequence: AB074162.

pleckstrin homology domain interacting protein:

| | | | | |
|---|---|---|---|---|
| AJ303102 | AL049321 | CH471051 | BX537762 | AF310250 |
| BI548935 | AL450327 | BC137488 | BC021905 | AK127816 |
| BC008909 | AK000712 | AL161957 | NM_017934 | CR600369 |
| BC036479 | BC064611 | BC081569 | DQ924532 | AK057039 |
| DA500781 | AK075124 | AL356776 | BC144670. | | oo20c08.x1 Soares_NSF_F8_9W_OT_PA_P_S1 *Homo sapiens* cDNA clone IMAGE:1566734 3, mRNA sequence: HS.134230.

*Homo sapiens* KIAA1045 (KIAA1045), mRNA: NM 015297.

*Homo sapiens* kelch domain containing 1 (KLHDC1), mRNA:

| | | | | |
|---|---|---|---|---|
| BC143597 | AK127202 | AK098735 | BC143596 | AL591767 |
| NM_172193 | BC101595 | BC031270 | BC101597 | AF111806 |
| AL833437 | CH471078. | | | |

*Homo sapiens* lipocalin 2 (LCN2), mRNA:

| | | | | |
|---|---|---|---|---|
| AK316217 | N79823 | CR542092 | CH471090 | BP272828 |
| X99133 | EU644752 | X83006 | S75256 | BX644845 |

| | | | | |
|---|---|---|---|---|
| BC033089 | NM_005564 | CA454137 | AL590708 | AW778875 |
| BM977724 | AK301694 | BF354583. | | |

*Homo sapiens* leucine-rich repeat-containing G protein-coupled receptor 6 (LGR6), transcript variant 3, mRNA:

| | | | |
|---|---|---|---|
| NM_001017404 | BC047905 | NM_001017403 | AK123055 |
| AK027377 | BM699180 | AF088074 | CH471067 |
| AY358119 | AF190501 | CQ840811 | NM_021636 |
| AB049405 | BC038795 | AB083616 | AL356953. |

PREDICTED: *Homo sapiens* misc_RNA (LOC100128771), miscRNA: XR_037860.1.

PREDICTED: *Homo sapiens* hypothetical protein LOC100129705 (LOC100129705), mRNA: XM_001723520.1.

PREDICTED: *Homo sapiens* similar to Fanconi anemia complementation group D2 protein (LOC100129929), mRNA: XM_001732829.1

PREDICTED: *Homo sapiens* misc_RNA (LOC100133075), miscRNA: XR_039086.1.

PREDICTED: *Homo sapiens* similar to hCG2024106, transcript variant 1 (LOC100134648), mRNA: XM_001724649.1.

PREDICTED: *Homo sapiens* misc_RNA (LOCI 00134669), miscRNA: XR_038059.1.

PREDICTED: *Homo sapiens* hypothetical protein LOC339047, transcript variant 74 (LOC339047), mRNA:

| | | | | |
|---|---|---|---|---|
| XM_001723375 | NM_178541 | AK124516 | BC039707 | AC137803 |
| BC046145 | BC008178 | AC138969 | AF229069 | BC010188 |
| AK126798 | AC136619. | | | |

PREDICTED: *Homo sapiens* similar to hCG1809904 (LOC391761), mRNA: XM_373073.2

PREDICTED: *Homo sapiens* similar to UDP-Gal:beta-GlcNAc beta 1,3-galactosyltransferase, polypeptide 4 (LOC402377), mRNA:

| | | |
|---|---|---|
| AL599456 | XR_079072 | BP872983 |
| BP872636 | AL161911. | |

PREDICTED: *Homo sapiens* hypothetical gene supported by AY007155 (LOC439949), mRNA:

| | | | |
|---|---|---|---|
| XM_001723825 | XM_001128367 | AY007155 | XM_001129241 |
| AL158043. | | | |

PREDICTED: *Homo sapiens* similar to MHC class II antigen (LOC642073), mRNA: XR_018080.2.

PREDICTED: *Homo sapiens* similar to hCG1730248 (LOC643037), mRNA:

| | | | |
|---|---|---|---|
| XM_926406 | AADB02014322 | AP000943 | XM_936787. |

PREDICTED: *Homo sapiens* region containing hypothetical protein LOC283970; similar to nuclear pore complex interacting protein, transcript variant 2 (LOC643943), mRNA: XM_934575.1.

PREDICTED: *Homo sapiens* hypothetical protein LOC645743 (LOC645743), mRNA: XM_928753.1.

PREDICTED: *Homo sapiens* similar to hCG1774990 (LOC646021), mRNA: XM_001718652.1

PREDICTED: *Homo sapiens* hypothetical LOC646498 (LOC646498), mRNA: NM_001080528 AC135506

PREDICTED: *Homo sapiens* similar to embigin homolog (LOC647121), mRNA:

| | | | | |
|---|---|---|---|---|
| AL592494 | AK128714 | NR_003955 | NM_198449 | AK300860 |
| AK304226 | AC035145 | CR625471 | U52054 | BC059398 |
| CR621536 | AC091833 | CH471123 | DC309453. | |

PREDICTED: *Homo sapiens* similar to Neuronal acetylcholine receptor protein, beta-4 subunit precursor (LOC649686), mRNA: XM_938759.1.

PREDICTED: *Homo sapiens* similar to Iduronate 2-sulfatase precursor (Alpha-L-iduronate sulfate sulfatase) (Idursulfase) (LOC653157), mRNA: XM_926258.1.

PREDICTED: *Homo sapiens* similar to Neutrophil defensin 1 precursor (HNP-1) (HP-1) (HP1) (Defensin, alpha 1) (LOC653600), mRNA: XM_928349.1.

PREDICTED: *Homo sapiens* misc_RNA (LOC728522), miscRNA: XR_015716.2.

PREDICTED: *Homo sapiens* similar to ring finger protein 18 (LOC732387), mRNA: XM_941859.1

*Homo sapiens* lactotransferrin (LTF), mRNA:

| | | | | |
|---|---|---|---|---|
| S52659 | M83205 | AY137470 | M83202 | AF332168 |
| AK303889 | CH471055 | AF508798 | U07643 | AK316330 |
| M73700 | AK292813 | DQ522304 | U95626 | DQ896102 |
| BC015823 | NM_002343 | X52941 | M18642 | BC015822 |
| DQ892855 | AY493417 | AY156717 | AK303995 | AY178998 |
| BC022347 | AY165046 | EU779935 | AK298035 | AK093852 |
| AY360320 | M93150 | X53961 | AK290859 | CD722125 |
| AY875691 | AC098613 | | | |

*Homo sapiens* methyltransferase like 7B (METTL7B), mRNA:

| | | | | |
|---|---|---|---|---|
| BC020509 | NM_152637 | AY358508 | AC009779 | CH471054 |
| CR595874 | AK290112 | | | |

*Homo sapiens* microRNA 940 (MIR940), microRNA: NR_030636.1: NR_030636.1.

*Homo sapiens* myeloperoxidase (MPO), nuclear gene encoding mitochondrial protein, mRNA:

| | | | | |
|---|---|---|---|---|
| S56200 | A08802 | Z37728 | M19507 | J02694M17170 |
| X15377 | M17173 | M17174 | M17171 | M17172 |
| M19508 | D14466 | M17175 | M17176 | AC004687 |
| BC130476 | X04876 | DQ088846 | CH471109 | X64647 |
| NM_000250. | | | | |

*Homo sapiens* myelin transcription factor 1-like (MYT1L), mRNA:

| | | | | |
|---|---|---|---|---|
| BC031690 | AL133024 | BC042833 | AB029029 | AB073885 |
| AC106046 | BC071612 | BF530661 | AC008276 | AC009232 |
| BM715930 | AF036943 | BF439754 | BC043230 | AC093390 |
| AC011301 | AK299571 | BC137273 | BC150281 | BC137272 |
| AK307797 | AC009471 | NM_015025 | BC109113. | |

PREDICTED: *Homo sapiens* neuroblastoma breakpoint family, member 1, transcript variant 16 (NBPF1), mRNA:

| | | |
|---|---|---|
| NM_001101663 | BC094705 | AK055895 |
| AL049742 | AF379606 | AK095030 |
| AF379607 | BC034418 | CR599564 |
| XM_002346226 | CR608846 | BC169317 |
| BC169318 | BC169316 | BC094841 |
| DB300232 | AF380582 | NM_001037675 |
| BC086308 | AL117237 | AF380580 |
| NM_183372 | BC063799 | BX546486 |
| BC027348 | AL592284 | NM_001039703 |
| AC026900 | AK302413 | AF379624 |
| NM_015383 | AF379626 | AF379627 |
| AF379628 | AK294944 | XM_001726946 |
| AK092351 | AF379620 | AF379621 |
| AF379622 | AF379623 | AK054850 |
| AL359176 | XM_001717398 | AF379615 |
| AF379616 | AF379613 | AF131738 |
| AF379614 | AL355149 | AF379619 |
| AL138796 | BX511041 | AK290302 |
| AF379617 | AL050141 | AF379618 |
| BC021111 | AF379611 | AF379612 |
| AY894574 | BC010124 | AY894573 |
| BC148331 | AY894572 | AL040349 |
| AY894571 | AY894570 | BC071995 |
| AY894579 | AY894578 | AY894577 |
| AL592307 | AY894576 | AY894575 |
| AL137798 | AK290142 | AI865471 |
| AF419617 | XM_001715810 | AF419616 |
| AF419619 | AF419618 | AK095459 |
| AF379632 | AY894583 | AF379631 |
| AL356004 | AY894582 | AF379634 |
| AY894585 | BC110431 | AF379630 |
| AY894581 | AK125792 | AY894580 |
| AL139152 | BC167783 | AK294414 |
| AF379635 | NM_017940 | AF420437 |
| BQ890458 | AK000726 | BC136292 |
| CR600619 | AL954711 | BC071723 |
| AF161426 | BI552657 | AB051480 |
| CR610345 | AK097180 | BC023087 |
| BX648497 | AL022240 | AL832622 |
| AB033071 | AY894561 | BC013805 |
| AY894563 | AY894562 | BC066930 |
| AY894565 | AY894567 | AY894566 |
| BX538005 | AY894569 | AY894568 |
| BX842679 | NM_173638 | DQ786323 |
| AK299360 | NM_001170755 | BC093404 |
| AK123260. | | |

*Homo sapiens* neuroblastoma breakpoint family, member 7 (NBPF7), mRNA: NM_001047980.1.

*Homo sapiens* 5'-nucleotidase domain containing 2 (NT5DC2), mRNA:

| | | | |
|---|---|---|---|
| DA013090 | DB265466 | AK022504 | CH471055 |
| AW510639 | BC047747 | DR003312 | AC112215 |
| CR612874 | BC014550 | BM982658 | NM_022908 |
| AK092469 | NM_001134231 | AF131781 | AK023995. |

*Homo sapiens* neurotrophin 3 (NTF3), mRNA:

| | | | | |
|---|---|---|---|---|
| AC137627 | BC107075 | X53655 | CH471116 | AC007848 |
| CN267386 | AK293895 | AW190653 | CD672441 | BC069773 |
| BU939830 | NM_002527 | M37763 | NM_001102654 | CR541906 |
| M61180. | | | | |

*Homo sapiens* phospholipase C-like 1 (PLCL1), mRNA:

| | | | | |
|---|---|---|---|---|
| D42108 | AC092599 | NM_001114661 | CH471063 | AC109589 |
| DA414853 | AC013478 | AC020719 | BC101531 | BP340710 |
| BX537442 | NM_006226 | BC111985 | DA193701 | AC011917 |
| T87219 | AK127514 | AK302673. | | |

*Homo sapiens* processing of precursor 5, ribonuclease P/MRP subunit (*S. cerevisiae*) (POPS), transcript variant 2, mRNA:

| | | | | |
|---|---|---|---|---|
| AJ306296 | CB995722 | AF070660 | CH471054 | AA918619 |
| AC063943 | BU155588 | AK223206 | BI668578 | BC012505 |
| NM_015918 | AK303144 | BI549018 | NM_198202 | CR625634 |
| AF117232. | | | | |

*Homo sapiens* PR domain containing 12 (PRDM12), mRNA:

| | | | | |
|---|---|---|---|---|
| NM_021619 | CH471090 | BC172255 | AY004252 | AL359092. |

*Homo sapiens* resistin (RETN), mRNA:

| | | | | |
|---|---|---|---|---|
| NM_020415 | BC069302 | AC008763 | BC101560 | DQ301958 |
| AF205952 | AY207314 | BC101554 | AF352730 | AF290874 |
| AY359066 | CH471139 | AF323081. | | |

*Homo sapiens* regulator of G-protein signaling 20 (RGS20), transcript variant 1, mRNA:

| | | | | |
|---|---|---|---|---|
| AF493940 | AC100821 | AC113194 | AF060877 | BC015614 |
| AK094503 | NM_003702 | AY046538 | CR622266 | BC063490 |
| CR602987 | CH471068 | AF074979 | NM_170587 | BC031328 |
| CR594448 | BC018618 | AF366057 | AF366056 | AF366055 |
| AF366054. | | | | |

*Homo sapiens* ribosomal protein L10-like (RPL10L), mRNA:

| | | | | |
|---|---|---|---|---|
| AK130863 | NM_080746 | AL591768 | AB063608 | BC066312 |
| AM392934 | AB063605 | CH471078 | BC014310. | |

*Homo sapiens* selenoprotein P, plasma, 1 (SEPP1), transcript variant 1, mRNA:

| | | | |
|---|---|---|---|
| BC058919 | Z11793 | AK094640 | NM_005410 |
| AC008945 | AK225801 | BC040075 | NM_001093726 |
| NM_001085486 | BC005244 | AL833145 | BI463468 |
| AK096125 | BC046152 | AK311392 | AU136519 |
| BC015875 | CR607609 | CH471119 | CR607105 |
| DQ022288 | BC030009. | | |

*Homo sapiens* splicing factor 1 (SF1), transcript variant 4, mRNA:

| | | | | |
|---|---|---|---|---|
| AP001462 | AK301803 | BC034451 | BQ230035 | CH471076 |
| AK296237 | AJ000052 | EU832634 | AJ000051 | BC000773 |
| L49345 | BC069273 | D26120 | EU832710 | BX095574 |
| D26121 | D26122 | AK293753 | BC008080 | AK299705 |
| BC011657 | BC008724 | BC038446 | BC032676 | BC020217 |
| NM_201995 | NM_201997 | Y08765 | NM_201998 | L49380 |
| Y08766 | CR600558 | NM_004630 | BU624935 | CR615439. |

*Homo sapiens* SH3-domain GRB2-like (endophilin) interacting protein 1 (SGIP1), mRNA:

| | | | | |
|---|---|---|---|---|
| AK125044 | BC040516 | AL139147 | NM_032291 | AL354978 |
| AL356913 | DA801276 | CH471059 | BX640813 | AB210039 |

-continued

| | | | | |
|---|---|---|---|---|
| CR622141 | AK298970 | EU831934 | AL136561 | AL391820 |
| AK090697 | AK299941 | AM392887 | CR749541 | EU832029. |

*Homo sapiens* SHC (Src homology 2 domain containing) transforming protein 3 (SHC3), mRNA:

| | | | | |
|---|---|---|---|---|
| D84361 | BC026314 | AL160054 | DQ896663 | AL353150 |
| NM_016848 | BX641139. | | | |

*Homo sapiens* solute carrier family 22 (organic cation transporter), member 2 (SLC22A2), mRNA:

| | | | | |
|---|---|---|---|---|
| NM_003058.2 | NM_003058 | BC039899 | CH471051 | AL162582 |
| AB075951 | X98333 | CR618035 | AK290787 | AJ251885 |
| BC030978. | | | | |

*Homo sapiens* solute carrier family 7 (cationic amino acid transporter, y+ system), member 5 (SLC7A5), mRNA:

| | | | | |
|---|---|---|---|---|
| CH471114 | AB018542 | NM_003486 | CR625513 | CR601601 |
| AM182888 | BC039692 | BC042600 | CR594130 | AB017908 |
| DQ896766 | AF077866 | DQ893338 | AB018009 | AB023721 |
| BC014177 | AC126696 | AF104032 | M80244 | BC114608. |

*Homo sapiens* solute carrier family 7 (cationic amino acid transporter, y+ system), member 6 (SLC7A6), transcript variant 2, mRNA:

| | | | | |
|---|---|---|---|---|
| CR623370 | BC028216 | AC020978 | NM_001076785 | DQ894203 |
| CR601248 | CR613948 | DQ891023 | CR749475 | AK310866 |
| AK311610 | D87432 | BP242589 | BC113100 | NM_003983 |
| CH471092 | CR606394 | AK310602 | CR592629 | CR749291. |

*Homo sapiens* small nucleolar RNA, C/D box 13 (SNORD13), small nucleolar RNA:

| | |
|---|---|
| NR_003041 | AC091144. |

*Homo sapiens* synaptophysin-like 1 (SYPL1), transcript variant 1, mRNA:

| | | | | |
|---|---|---|---|---|
| BG719851 | CH471070 | NM_182715 | AK292230 | CB989012 |
| BQ429369 | X68194 | BC020938 | X61382 | EU831812 |
| NM_006754 | S72481 | AA969654 | BC061887 | BC016835 |
| AC005095 | CR616230 | AK128279 | CH236947 | EU831889. |

*Homo sapiens* tripartite motif-containing 34 (TRIM34), transcript variant 2, mRNA:

| | | | |
|---|---|---|---|
| AK293295 | NM_130390 | BC156770 | DA847894 |
| BM989990 | AK027664 | AF220144 | BG721109 |
| AF220143 | AC015691 | NM_001003827 | BG776117 |
| BC140722 | AK298301 | NM_021616 | CX760618 |
| CR624250 | AK023210 | CR749260 | AK316289 |
| BC065575 | AK290172 | BC136871 | NM_130389 |
| AL583914 | CH471064 | BC047564 | NM_001003818 |
| NM_001003819 | NM_058166 | AK316178 | AB039903 |
| AB039902 | AK027876 | AF220030 | AB039904. |

*Homo sapiens* V-set and transmembrane domain containing 2A (VSTM2A), mRNA: NM_182546.2.

Homo sapiens zinc finger protein 461 (ZNF461), mRNA:

| | | | | |
|---|---|---|---|---|
| NM_153257 | AB209279 | AB021641 | BC028631 | AY329493 |
| BX649031 | AK292834 | DQ894367 | AK299370 | AC074138 |
| DQ891185. | | | | |

Homo sapiens zinc finger protein 485 (ZNF485), mRNA:

| | | | | |
|---|---|---|---|---|
| CQ783574 | BC014161 | NM_145312 | AK074679 | AL645634 |
| CH471160 | BX648149 | AK313328 | AK299707. | |

PREDICTED: Homo sapiens misc_RNA (ZNF788), misc-RNA: XR_041527.1.

Homo sapiens zinc finger protein 830 (ZNF830), mRNA: NM_052857.3.

PREDICTED: Homo sapiens zinc finger protein 90 (HTF9) (ZNF90), mRNA:

| | | | | |
|---|---|---|---|---|
| CR614976 | NM_007138 | CN386341 | BC137211 | CR593334 | AC006539 |
| CH471106 | AK298173 | AC011447 | BX102781 | M61870. | |

Homo sapiens alkaline phosphatase, liver/bone/kidney (ALPL), transcript variant 1, mRNA:

| | | | | |
|---|---|---|---|---|
| AL592309 | AB011406 | BC066116 | AB012643 | BC136325 |
| NM_000478 | NM_001127501 | AL359815 | X53750 | BC021289 |
| AB209814 | D87880 | D87882 | D87881 | AK298085 |
| M24429 | BC126165 | M24428 | BC110909 | D87877 |
| D87887 | D87876 | CH471134 | D87888 | D87879 |
| D87889 | D87878 | D87883 | AK312667 | D87884 |
| DA625627 | D87875 | D87885 | D87874 | D87886 |
| DA631560 | M24435 | M24434 | M24433 | M24432 |
| BC090861 | M24431 | M24430 | AK293184 | M24439 |
| M24438 | M24437 | M24436 | AK295608 | X14174 |
| AK097413. | | | | |

Homo sapiens interleukin 8 receptor, beta (IL8RB), mRNA:

| | | | | |
|---|---|---|---|---|
| U11869 | DA670033 | U11866 | AK290906 | DQ895671 |
| NM_001168298 | DA674925 | L19593 | AB032733 | AC124768 |
| AB032734 | U11873 | U11872 | DQ893661. | |

Example 2: Determination of Selected Biomarkers by Reverse Transcriptase (RT) and Droplet Digital Polymerase Chain Reaction (ddPCR)

In the prior example, 5 patients were categorized as lower respiratory infections (LRI), but analysis of the case reports indicates that the patients with the lowest biomarker levels, especially DEFA1, were actually unlikely to have had a pulmonary infection. One patient clearly had a pulmonary embolism (PE) secondary to air travel, and another subject was actually a healthcare worker with a mild upper respiratory (UR) condition that could have been allergic.

In order to determine more fully whether the biomarkers had value in detecting pulmonary infections, 4 additional subjects were obtained, and they were compared with 3 subjects with known hernias, surgically confirmed, and 5 subjects presenting for coronary catheterization but no known pulmonary infection or distress. The 2 patients from Example 1 with PE and UR condition were excluded, because they were not, in fact, suspected LRI/pneumonia, yielding 7 suspected LRI, and 8 control subjects.

Methods: The Tempus blood RNA preservative tubes were frozen at −80 C as in prior studies, and then thawed and total nucleic acid was isolated by the manufacturer's protocol. The total nucleic acids were treated with DNAse, as above, and the remaining RNA was concentrated and quantified as above. A specific amount of RNA (500 ng) was taken into a reverse transcriptase (RT) reaction using Bio-Rad iScript (RNAse H+) with random hexamers primers, according to the manufacturer's procedure. From the RT reaction, the resulting cDNA was diluted 1:15 with water to make a stock cDNA solution from each patient for further analysis. The stock cDNA from each patient was diluted 1:10 or 1:20 into the PCR reaction and mixed with reagents for ddPCR as specified by the manufacturer. In ddPCR, the RNA strands in aqueous solution are emulsified in oil diluent to create 'droplets' of extremely small volumes of aqueous solution such that, on average, only a single strand of any particular RNA will be contained within each droplet. Each droplet also contains polymerase, nucleotides, and the specific primers that are employed to quantify a specific RNA target (eg DEFA1) and a fluorochrome that detects the PCR amplimer (EvaGreen), thus making each droplet a small reaction vessel for PCR amplification. Any droplet that contain a DEFA1 RNA transcript will produce a positive fluorescent droplet, while droplets that are negative for DEFA1 will produce little or no fluorescence. Thus, the number of positive droplets will be directly proportional to the absolute quantity of the RNA target in the sample and can be calculated using Bayesian statistics and a Poisson distribution.

The ddPCR analysis was conducted on the 7 suspected LRI, and 8 control subjects, using 3 biomarkers (DEFA1, ALPL, IL8RB) and one invariant control (ACTB). The ALP, and IL8RB markers are included here because the lungs can also be affected by biofilm infections, although that could not be determined in the present 7 suspected LRI subjects. Thus, DEFA1 is the exemplary biomarker that should be sensitive to a pulmonary infection. The absolute quantity of the transcripts was quantified by ddPCR and then corrected for any dilutions that were employed (10× or 20×), and then the levels of the biomarkers were expressed as a % of ACTB invariant control level for each sample.

Results: As shown in FIG. 1, the level of the DEFA1 biomarker is markedly higher in suspected LRI/pneumo patients (n=7) versus non-LRI controls (n=8) (LRI=81.6%, (sem=42.4), vs Con=8.6% (3.0%), t-test p<0.05). Likewise, the ALPL biomarker was also higher in LRI than controls, (LRI=2.7/(0.6%) vs Con=0.7% (0.09%), p<0.01). Neither IL8RB (LRI=6.0% (1.5%) vs Con-6.6% (1.0%), p>0.35), nor the combination of ALPL+IL8RB (LRI=8.7% (1.4%) vs Con=7.2% (1.1%), p>0.20) was significantly different between groups. Two of the subjects with suspected pneumonia showed relatively normal DEFA1 levels and so their charts were reviewed. In one case, it was discovered that the patient had been on antibiotics for 7 days prior to admission and blood sampling, and in the other case, the patient had pneumonitis due to amiodarone toxicity, with a cough, fever, and apparent infiltrates on X-ray, but showed a normal white blood cell count and had negative bacterial cultures, suggesting that the patient may not have had an active pulmonary infection at the time of sampling, although the clinical suspicion was reasonable.

Example 3: Other Embodiments of a Neutrophil Activation Test for Respiratory Infections These further embodiments utilize the RNA and protein biomarkers disclosed in Examples 1 and 2 above, and disclose alternative methods by which they could be quantified in clinically relevant instances for humans and other living species.

Identification of RNA Biomarkers in Immune Cells without the Need for Lysis and RNA Purification There is a huge, worldwide, unmet medical need for a simple, rapid, inexpensive test that reports whether the patient's immune system is responding to a pathogen. In the U.S., some of this diagnostic need is fulfilled with advanced imaging tests, such as X-rays, CT, and MRI, but in developing countries, and rural areas of developed nations, diagnostic tools are limited to a thermometer, stethoscope, and possibly a white cell count.

A cell-based assay. In one embodiment of the present invention, termed 'cell-based assay', the said biomarkers would be quantitated on cells, or cell fractions derived from the biological sample. The biological sample would include any samples previously described, such as blood, sputum, lavage, spinal fluid, etc, but the method of biomarker determination would not require the lysis of the cells contained therein. Rather, the cells within the sample would be captured by any of a variety of means known to persons skilled in the art, and then the RNA or protein levels of said biomarkers would be quantitated on the cells directly. In this method, the cells can be captured with, or without centrifugation, which has significant advantages because centrifugation is not always available in non-hospital settings. Further, the number of cells required would be quite small, for instance in the range of 10,000 cells, which can be obtained from just microliters of blood. Venipuncture is painful and distressing, especially to children, and so a finger stick would be better tolerated, but still provide an adequate sample of cells for analysis.

The overall design of the test is to conduct the cell-based assay on small volumes of blood, such as obtained from a venipuncture or finger stick. In one embodiment, the blood is drawn via capillary action into a flat chamber, which is separated into several smaller chambers. We disclose herein an exemplary method using just 2 cells types, neutrophils and T cells. Other types of cells can also be used. In one embodiment of the invention, each flow chamber is coated with specific antibodies to surface markers for neutrophils (CD16b) or T cells (CD4) so that the desired cell is trapped by adhesion in that well [3; 4]. After an incubation period of about 10-20 minutes, the unbound cells are flushed away with buffer contained in the fluidic pack.

Biomarker detection. As described, any of a variety of conventional methods are used to immobilize cell-specific antibodies on a glass coverslip or other suitable surface to capture cells from whole blood or other relevant biological samples. After washing away unbound cells, the bound cells are contacted with any of the analytical tools described for measuring the specific biomarkers, such as, for example, resistins (RSTN), defensins (DEFA1), and myeloperoxidases (MPO). These analytical detection methods share the common trait that they bind to the target biomarker, and produce a detectable signal when bound to the biomarker.

Engineering: Any handheld automated microfluidic device and a smartphone based imager can be adapted for use in a method as described herein [5; 6]. Suitable commercially available devices can also be used.

Bioinformatic: Once the handheld imager captures the detectable signal of said biomarkers in the cells, where for example the signal is DEFA1 mRNA level, it is then simple integration to compute the signal intensity per cell and ratio the level to the invariant control (e.g., ACTB). Because multiple channels can be used, or multiple signals on the same channel, it is clear that multiple biomarkers can be quantitated on the same biological sample. In such a case, the biological markers could be combined to create a metric of neutrophil activation, such as, (RSTN+DEFA1+MPO)/ACTB=neutrophil activation level.

Alternatively or in addition, a ligase-based assay can be used to quantitate the RNA levels in suitable samples. Likewise, it is technically feasible to conduct RNA or cDNA sequencing reactions within cells, as described in the scientific literature.

Instead of, or in addition to, assays using RNA markers, either the level of protein or protein enzymatic activity can be used as the biomarker. For example, the cell-based assay described above can be adapted to detect RSTN or DEFA1 protein level, by a fluorescent antibody, or an enzymatic activity such MPO activity. Because separate chambers can be used for each type of reaction, one embodiment employs a hybrid test in which, for example, RSTN RNA is detected in one chamber, DEFA1 antigen in another, and MPO activity in a third. This can be accomplished without the need for obtaining additional clinical samples.

REFERENCES FOR BACKGROUND AND EXAMPLES

1. Lozano R Naghavi M Foreman K Lim S Shibuya K Aboyans V Abraham J Adair T Aggarwal R Ahn S Y et al. 2012. Global and regional mortality from 235 causes of death for 20 age groups in 1990 and 2010: a systematic analysis for the Global Burden of Disease Study 2010. *Lancet* 380(9859): 2095-2128.
2. Toma I, Siegel M O, Keiser J, Yakovieva A, Kim A, Davenport L, Devaney J, Hoffman E P, Alsubail R, Crandall K A et al. 2014. Single-Molecule Long-Read 16S Sequencing To Characterize the Lung Microbiome from Mechanically Ventilated Patients with Suspected Pneumonia. *J Clin Microbiol* 52(11): 3913-3921.
3. Sekine K. 2006. Panning of multiple subsets of leukocytes on antibody-decorated poly(ethylene) glycol-coated glass slides. *Journal of immunological methods* 313(1-2): 96-109.
4. Sethu P, Moldawer L L, Mindrinos M N, Scumpia P O, Tannahill C L, Wilhelmy J, Efron P A, Brownstein B H, Tompkins R G, Toner M. 2006. Microfluidic isolation of leukocytes from whole blood for phenotype and gene expression analysis. *Anal Chem* 78(15): 5453-5461.
5. Li B, Li L, Guan A, Dong Q, Ruan K, Hu R, Li Z. 2014. A smartphone controlled handheld microfluidic liquid handling system. *Lab Chip* 14(20): 4085-4092.
6. Li Z. 2014. Miniature optofluidic darkfield microscope for biosensing. *SPIE Ultrafast Nonlinear Imaging and Spectroscopy* 9815: 15.
7. Almansa R, Socias L, Sanchez-Garcia M, Martin-Loeches I, del Olmo M, Andaluz-Ojeda D, Bobillo F, Rico L, Herrero A, Roig V et al. 2012. Critical COPD respiratory illness is linked to increased transcriptomic activity of neutrophil proteases genes. *BMC Res Notes* 5: 401.
8. Jendeberg A L, Stralin K, Hultgren O. 2013. Antimicrobial peptide plasma concentrations in patients with community-acquired pneumonia. *Scand J Infect Dis* 45(6): 432-437.
9. Berkestedt I, Herwald H, Ljunggren L, Nelson A, Bodelsson M. 2010. Elevated plasma levels of antimicrobial polypeptides in patients with severe sepsis. *J Innate Immun* 2(5): 478-482.

10. Bostrom E A, Tarkowski A, Bokarewa M. 2009. Resistin is stored in neutrophil granules being released upon challenge with inflammatory stimuli. *Biochim Biophys Acta* 1793(12): 1894-1900.
11. Macdonald S P, Stone S F, Neil C L, van Eeden P E, Fatovich D M, Arendts G, Brown S G 2014. Sustained elevation of resistin, NGAL and IL-8 are associated with severe sepsis/septic shock in the emergency department. *PLoS One* 9(10): e110678.
12. Johansson L, Linner A, Sunden-Cullberg J, Haggar A, Herwald H, Lore K, Treutiger C J, Norrby-Teglund A. 2009. Neutrophil-derived hyperresistinemia in severe acute streptococcal infections. *J Immunol* 183(6): 4047-4054.
13. Kunnari A M, Savolainen E R, Ukkola O H, Kesaniemi Y A, Jokela M A. 2009. The expression of human resistin in different leucocyte lineages is modulated by LPS and TNFalpha. *Regul Pept* 157(1-3): 57-63.
14. Lundergan C, Burke H, McCaffrey T. 2009. Prediction of bare metal stent restenosis. U.S. Pat. No. 7,550,300. CapGen Sciences, Inc., United States.
15. Li B, Li Z. 2014. Handheld microfluidic liquid handling system. In US Patent Office.
16. Li Z, Scherer A. 2014. Handheld low pressure mechanical cell lysis device with single cell resolution. In US Patent Application.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding embodiments are to be construed as merely illustrative, and not limiting of the scope of the invention in any way whatsoever. Those skilled in the art will recognize, or be able to ascertain using no more than routine experimentation, numerous equivalents to the compositions and methods of use thereof described herein. Such equivalents are considered to be within the scope of this invention and are covered by the following claims. Those skilled in the art will also recognize that all combinations of embodiments described herein are within the scope of the invention.

We claim:

1. A method of diagnosing a lower respiratory infection in a subject, comprising:
    obtaining a biological sample from said subject;
    detecting expression levels of a plurality of biomarkers in the biological sample, wherein the plurality of biomarkers comprise alkaline phosphatase liver isoform (ALPL), interleukin-8 receptor-beta (IL8RB), and Defensin alpha 1;
    determining the expression levels of said plurality of biomarkers by comparing the expression levels of said plurality of biomarkers to at least one control marker;
    correlating the determined expression levels of said plurality of biomarkers with the occurrence of a lower respiratory infection in the subject; and
    following the correlating step, treating the subject for a lower respiratory infection
    comprising at least one of administering antibiotics to said subject, administering antivirals to said subject, and administering anti-inflammatories to said subject.
2. The method of claim 1, further comprising calculating a biomarker infection score from said determined expression levels of said plurality of biomarkers and comparing said biomarker infection score to a control score.
3. The method of claim 1, wherein said determining the expression levels of said plurality of biomarkers and said at least one control marker comprises using a multivariate prediction model to determine if a pattern of expression of said plurality of biomarkers is indicative of a lower respiratory infection.
4. The method of claim 1, wherein said biological sample is a blood sample.
5. The method of claim 4, wherein said obtaining a biological sample further comprises isolating immune cells from said blood sample.
6. The method of claim 5, wherein said immune cells are neutrophils, T-cells, or a combination thereof.
7. The method of claim 1, wherein said detecting expression levels of a plurality of biomarkers comprises measuring RNA levels of said plurality of biomarkers.
8. The method of claim 7, wherein measuring RNA levels comprises using fluorescently-labeled probes complementary to the said plurality of biomarkers, a ligase-based assay, reverse transcriptase and polymerase chain reaction, RNA sequencing, or cDNA microarray.
9. The method of claim 1, wherein said at least one control marker is actin-beta (ACTB).
10. A method of treating a lower respiratory infection in a subject, comprising:
    obtaining a biological sample from said subject;
    detecting expression levels of a plurality of biomarkers in the biological sample, wherein the plurality of biomarkers comprise alkaline phosphatase liver isoform (ALPL), interleukin-8 receptor-beta (IL8RB), and Defensin alpha 1;
    determining the expression levels of said plurality of biomarkers by comparing the expression levels of said plurality of biomarkers to at least one control marker;
    correlating the determined expression levels of said plurality of biomarkers with the occurrence of a lower respiratory infection in the subject; and
    following the correlating step, treating the subject for a lower respiratory infection
    comprising at least one of administering antibiotics to said subject, administering antivirals to said subject, and administering anti-inflammatories to said subject.
11. The method of claim 10, further comprising calculating a biomarker infection score from said determined expression levels of said plurality of biomarkers and comparing said biomarker infection score to a control score.
12. The method of claim 10, wherein said determining the expression levels of said plurality of biomarkers comprises using a multivariate prediction model to determine if a pattern of expression of said plurality of biomarkers is indicative of a lower respiratory infection.
13. The method of claim 10, wherein said biological sample is a blood sample.
14. The method of claim 13, wherein said obtaining a biological sample further comprises isolating immune cells from said blood sample.
15. The method of claim 14, wherein said immune cells are neutrophils, T-cells, or a combination thereof.
16. The method of claim 10, wherein detecting expression levels of the plurality of biomarkers comprises measuring RNA levels of said plurality of biomarkers.
17. The method of claim 16, wherein measuring RNA levels comprises using fluorescently-labeled probes complementary to said plurality of biomarkers, a ligase-based assay, reverse transcriptase and polymerase chain reaction, RNA sequencing or cDNA microarray.

18. The method of claim 10, wherein said at least one control marker is actin-beta (ACTB).

19. A method of treating a lower respiratory infection in a subject comprising:
  obtaining a biological sample from said subject;
  contacting the biological sample from said subject with first agents that are present in a kit for use in diagnosing a lower respiratory infection in a subject;
  detecting binding of the first agents to a plurality of biomarkers in the biological sample to thereby determine the expression levels of the plurality of biomarkers, wherein the plurality of biomarkers comprise alkaline phosphatase liver isoform (ALPL), interleukin-8 receptor-beta (IL8RB), and Defensin alpha 1;
  comparing the expression levels if the plurality of biomarkers to at least one control marker;
  correlating the compared expression levels of said plurality of biomarkers with the occurrence of a lower respiratory infection in the subject; and
  following the correlating step, treating the subject for a lower respiratory infection comprising administering antibiotics to said subject, administering antivirals to said subject, or administering anti-inflammatories to said subject,
  wherein said kit comprises:
  first agents that specifically bind to the plurality of biomarkers;
  second agents that specifically bind to at least one control marker;
  instructions for use of the agents for determining an increase or decrease in the expression levels of said plurality of biomarkers by comparing the expression levels of said plurality of biomarkers to said at least one control marker; and
  instructions for correlating the expression levels of said plurality of biomarkers to the occurrence of a lower respiratory infection.

* * * * *